US010035994B2

(12) United States Patent
Pogue et al.

(10) Patent No.: US 10,035,994 B2
(45) Date of Patent: *Jul. 31, 2018

(54) PLANT-BASED RECOMBINANT BUTYRYLCHOLINESTERASE PRODUCTION METHODS

(71) Applicants: Kentucky BioProcessing, Inc., Winston-Salem, NC (US); Tsafrir Mor, Tempe, AZ (US)

(72) Inventors: Greg Pogue, Austin, TX (US); Ernie Hiatt, Maceo, KY (US); Romy Kandzia, Halle (DE); Stefan Werner, Halle (DE); Frank Thieme, Halle (DE); Tsafrir Mor, Tempe, AZ (US); Steven Hume, Owensboro, KY (US)

(73) Assignee: KENTUCKY BIOPROCESSING, INC., Winston-Salem, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/602,622

(22) Filed: May 23, 2017

(65) Prior Publication Data

US 2017/0313999 A1 Nov. 2, 2017

Related U.S. Application Data

(62) Division of application No. 14/448,545, filed on Jul. 31, 2014, now Pat. No. 9,688,970.

(60) Provisional application No. 61/885,492, filed on Oct. 1, 2013.

(51) Int. Cl.
*C12N 9/18* (2006.01)
*A61K 38/46* (2006.01)

(52) U.S. Cl.
CPC ............. *C12N 9/18* (2013.01); *A61K 38/465* (2013.01); *C12Y 301/01008* (2013.01)

(58) Field of Classification Search
None
See application file for complete search history.

(56) References Cited

U.S. PATENT DOCUMENTS

| 8,729,245 B2 | 5/2014 | Yim et al. |
| 2012/0207738 A1 | 8/2012 | Rosenberg |
| 2013/0156749 A1 | 6/2013 | Rosenberg |

FOREIGN PATENT DOCUMENTS

| WO | 2014153253 | 9/2014 |

OTHER PUBLICATIONS

Geyer et al. (Transgenic plants as a source for the bioscavenging enzyme, human butyrylcholinesterase, Plant Biotechnology Journal (2010) 8, pp. 873-886).*

The United States Patent and Trademark Office; The International Search Report and the Written Opinion of the International Searching Authority for PCT/US14/49387; dated Jan. 16, 2015; pp. 1-14; The United States Patent and Trademark Office; U.S.A.
Schneider, et al.; Expression of human butyrylcholinesterase with an engineered glycosylation profile resembling the plasma-derived orthologue; journal article; 2014; pp. 501-510; Biotechnology Journal; vol. 9; copyright 2013 Wiley-VCH Verlag GmbH & Co. KGaA, Weinheim; www.biotechnology-journal.com.
Schneider, et al.; Oligomerization status influences subcellular deposition and glycosylation of recombinant butyrylcholinesterase in Nicotiana benthamiana; journal article; 2014; pp. 832-839; Plant Biotechnology Journal; vol. 12; copyright 2014 The Authors; Published by Society for Experimental Biology and the Association of Applied Biologists and John Wiley & Sons Ltd.
Larrimore, et al.; Plants as a source of butyrylcholinesterase variants designed for enhanced cocaine hydrolase activity; journal article; 2013; pp. 217-220; Chemico-Biological Interactions; vol. 203; copyright 2012 Elsevier Ireland Ltd.; www.elsevier.com.
Geyer, et al.; Reversal of Succinylcholine Induced Apnea with an Organophosphate Scavenging Recombinant Butyrylcholinesterase; article; Mar. 2013; PLoS ONE; pp. 1-6; vol. 8; issue 3; www.plosone.org.
Castilho, et al.; Construction of a Functional CMP-Sialic Acid Biosynthesis Pathway in *Arabidopsis*; article; 2008; pp. 331-339; vol. 147; published in Plant Physiology; copyright 2008 American Society of Plant Biologists; www.plantphysiol.org; USA.

(Continued)

*Primary Examiner* — Suzanne M Noakes
*Assistant Examiner* — Jae W Lee
(74) *Attorney, Agent, or Firm* — Wyatt, Tarrant & Combs, LLP; Stephen C. Hall; Max E. Bridges

(57) ABSTRACT

A new, reliable, easily scalable and reproducible method for the production of recombinant butyrylcholinesterase (rBuChE) is provided. Through the utilization of a plant transfection procedure, various plant strains have been shown to generate effective and scalable amounts of rBuChE under acceptable manufacturing processes to permit reliable levels of such enzymes for desired nerve agent protection requirements (including tetrameric products). As well, such methods in engineered plant lines have shown suitable production of these enzymes in tetramer form with glycan formation and sialylation (for terminal groups) to allow for optimal potency against organophosphorus agent exposure as well as proper immunogenic response within the plant sources. The overall production method, including the transfection and production within mammalian cells, as well as the process steps involved for such a reliable sourcing platform from plants is thus encompassed within the invention.

20 Claims, 25 Drawing Sheets

(3 of 25 Drawing Sheet(s) Filed in Color)

(56) References Cited

OTHER PUBLICATIONS

Castilho, et al.; In Planta Protein Sialylation through Overexpression of the Respective Mammalian Pathway; Journal article; May 21, 2010; pp. 15923-15930; vol. 285; No. 21; published in the Journal of Biological Chemistry; copyright 2010 The American Society for Biochemisty and Molecular Biology, Inc.; USA.

Castilho, et al.; N-Glycosylation engineering of plants for the biosynthesis of glycoproteins with bisected and branched complex N-glycans; article; Feb. 11, 2011; pp. 813-823; vol. 21; No. 6; published in Glycobiology; http://glycob.oxfordjournals.org; published by Oxford University Press.

Castilho, et al.; Humanization of the plant N-glycosylation pathway for the production of therapeutically relevant proteins; journal article; 2011; p. 240; vol. 28; published in Glycoconjugate J.

Diaz, et al.; Sensitive and Specific Detection of the Non-Human Sialic Acid N-Glycolylneuraminic Acid in Human Tissues and Biotherapeutic Products; journal article; Jan. 2009; e4241; vol. 4; issue 1; Published in PLoS ONE; www.plosone.org.

Duysen, et al.; Wild-Type and A328W Mutant Human Butyrylcholinesterase Tetramers Expressed in Chinese Hamster Ovary Cells Have a 16-Hour Half-Life in the Circulation and Protect Mice from Cocaine Toxicity; journal article; Jan. 29, 2002; pp. 751-758; vol. 302; No. 2; published in The Journal of Pharmacology and Experimental Therapeutics; copyright 2002 by The American Society for Pharmacology and Experimental Therapeutics; USA.

Ellman, et al.; Colorimetric determination of cholinesterase activity; essay; Jul. 1961; pp. 88-95; vol. 7; Biochem Pharmacol; Analytical Chemistry; http://www.ihop-net.org/UniPub/iHOP/gs/1357838.html.

Engler, et al.; A One Pot, One Step, Precision Cloning Method with High Throughput Capability; journal article; Nov. 2008; e3647; vol. 3; issue 11; Published in PLoS ONE; www.plosone.org.

Giritch, et al.; Rapid high-yield expression of full-size IgG antibodies in plants coinfected with noncompeting viral vectors; journal article; 2006; pp. 14701-14706; vol. 103; No. 40; published in the Proceedings of the National Academy of Sciences of the United States of America; www.pnas.org; USA.

Geyer, et al.; Plant-derived human butyrylcholinesterase, but not an organophosphorous-compound hydrolyzing variant thereof, protects rodents against nerve agents; journal article; Nov. 23, 2010; pp. 20251-20256; vol. 107; No. 47; published in the Proceedings of the National Academy of Sciences of the United States of America; www.pnas.org; USA.

Gleba, et al.; Magnifection—a new platform for expressing recombinant vaccines in plants; article; 2005; pp. 2042-2048; Vaccine 23; published in Elsevier; www.elsevier.com/locate/vaccine.

Gleba, et al.; Viral vectors for the expression of proteins in plants; opinion; 2007; pp. 134-141; vol. 18; published in Biotechnology; published in Elsevier; www.sciencedirect.com.

Li, et al.; Lamellipodin proline rich peptides associated with native plasma butyrylcholinesterase tetramers; journal article; 2008; pp. 425-432; vol. 411; published in Biochemical Journal; Great Britain.

Weber, et al.; A Modular Cloning System for Standardized Assembly of Multigene Constructs; journal article; Feb. 2011; e16765; vol. 6; issue 2; Published in PLoS ONE; www.plosone.org.

Werner, et al.; Fast track assembly of multigene constructs using Golden Gate cloning and the MoClo system; journal article; 2012; published in Bioengineered Bugs; pp. 38-43; vol. 3; issue 1.

Fischer, et al; Sialic acid-binding lectins: submolecular specificity and interaction with sialoglycoproteins and tumour cells; journal article; 1995; pp. 707-713; Glycoconjugate Journal; vol. 12; copyright 1995 Chapman & Hall.

Lockridge, et al; Large Scale Purification of Butyrylcholinesterase From Human Plasma Suitable for Injection Into Monkeys; A Potential New Therapeutic for Protection Against Cocaine and Nerve Agent Toxicity; author manuscript; J Med Chem Biol Radiol Def. Jul. 1, 2005; NIH (National Institutes of Health) Public Access; pp. 2-23.

US-FDA/USDA Guidance for Industry: Drugs, Biologics, and Medical Devices Derived from Bioengineered Plants for Use in Humans and Animals; guidance; pp. 1-30; http://www.fda.gov/downloads/Drugs/GuidanceComplianceRegulatoryInformation/Guidances/ucm124811.pdf, accessed May 30, 2013.

Huang, et al.; Recombinant human butyrylcholinesterase from milk of transgenic animals to protect against organophosphate poisoning; journal article; Aug. 21, 2007; pp. 13603-13608; vol. 104; No. 34; published in the Proceedings of the National Academy of Sciences of the United States of America; www.pnas.org; USA.

Kolarich, et al.; Glycoproteomic characterization of butyrylcholinesterase from human plasma; research article; 2008; pp. 254-263; vol. 8; copyright 2008 Wiley-VCH Verlag GmbH & Co. KGaA, Weinheim; www.proteomics-journal.com.

Singh, et al.; Microbial degradation of organophosphorus compounds; journal article; 2006; pp. 428-471; FEMS Microbiol Rev vol. 30; copyright 2006 Federation of European Microbiological Societies; published by Blackwell Publishing Ltd.; http://femsre.oxfordjournals.org.

Pogue, et al.; Production of pharmaceutical-grade recombinant aprotinin and a monoclonal antibody product using plant-based transient expression systems; journal article; 2010; pp. 638-654; Plant Biotechnology Journal; vol. 8; copyright 2010 The Authors; copyright (journal compilation) 2010 Blackwell Publishing Ltd.

Ross, et al.; Nerve Agent Bioscavenger: Development of a New Approach to Protect Against Organophosphorus Exposure; book; 2008; pp. 243-257; chapter 7; Medical Aspects of Chemical Warfare.

Otto, et al.; Dramatic Differences in Organophosphorus Hydrolase Activity between Human and Chimeric Recombinant Mammalian Paraoxonase-1 Enzymes; article; 2009; pp. 10416-10422; Biochemistry 2009; vol. 48; No. 43; pubs.acs.org/Biochemistry; copyright 2009 American Chemical Society.

Ilyushin, et al.; Chemical polysialylation of human recombinant butyrylcholinesterase delivers a long-acting bioscavenger for nerve agents in vivo; journal article; Jan. 7, 2013; pp. 1-6; published in the Proceedings of the National Academy of Sciences of the United States of America; www.pnas.org; USA.; www.pnas.org.

Skretas, G., et al.; Expression of active human sialyltransferase ST6GalNAcl in *Escherichia coli*; 11 pages; Microbial Cell Factories; 2009, vol. 8, No. 50.

Geyer, B.C., et al.; Transgenic plants as a source for the bioscavenging enzyme, human butyrylcholinesterase; 2010; pp. 873-886; Plant Biotechnology Journal, vol. 8.

Biberoglu, K., et al.; The proline-rich tetramerization peptides in equine serum butyrylcholinesterase; 2012; pp. 3844-3858; The FEBS Journal; vol. 279.

Castilho, A., et al.; Generation of biologically active multi-sialylated recombinant human EPOFc in plants; 2013; PLoS ONE; vol. 8, No. 1; e54836, doi: 10.1371/journal.pone.0054836.

Schillberg, S., et al.; Molecular farming of pharmaceutical proteins using plant suspension cell and tissue cultures; 2013; pp. 5531-5542; Current Pharmaceutical Design; vol. 19.

Wolfson, W., et al.; Grow your own: Protalix BioTherapeutics produces drugs in carrot cells; 2013; pp. 969-970; Chemistry & Biology; vol. 20.

Ngamelue, et al.; Crystallization and X-ray structure of full-length recombinant human butyrylcholinesterase; manuscript from Acta Crystallographica Section F Structural Biology and Crystallization Communications; vol. 63.; No. 3; 2007; pp. 723-727.

Saxena, et al.; Structure of Glycan Moeties Responsible for the Extended Circulatory Life Time of Fetal Bovine Serum Acetylcholinesterase and Equine Serum Butyrylcholinesterase; Biochemistry; vol. 36, No. 24, 1997; pp. 1481-7489.

Huang, et al.; Substantially improved pharmacokinetics of recombinant human butyrylcholinesterase by fusion to human serum albumin; BMC Biotechnology; 8:50; 2008; pp. 1-11; http://www.biomedcentral.com/1472-6750/8/50.

* cited by examiner

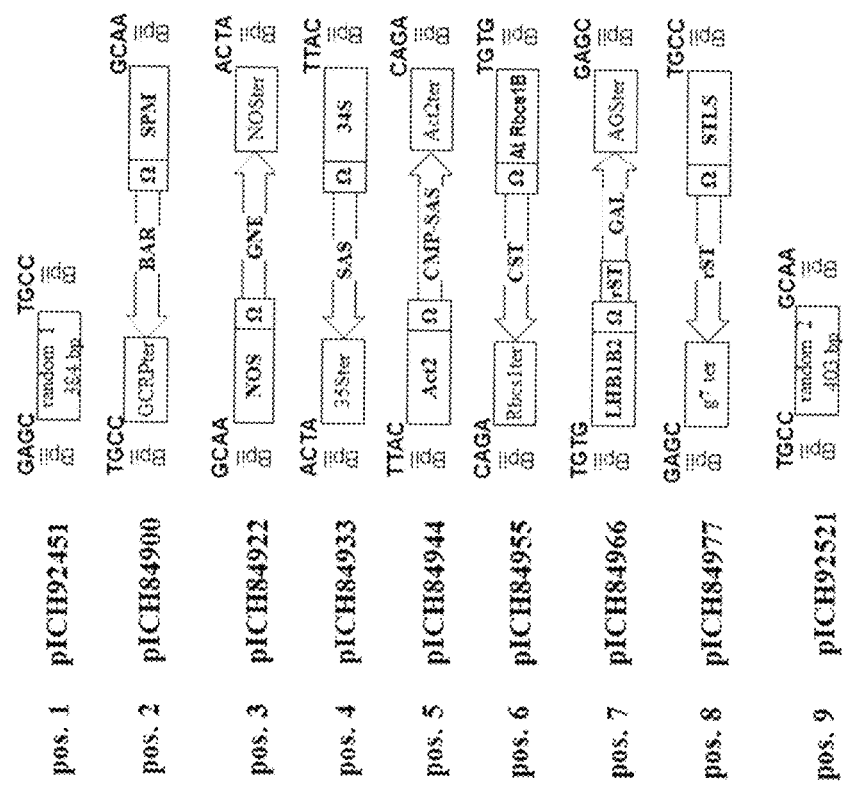
Figure 4.A – Assembly of multigene construct pICH88266, Level 1 expression cassettes

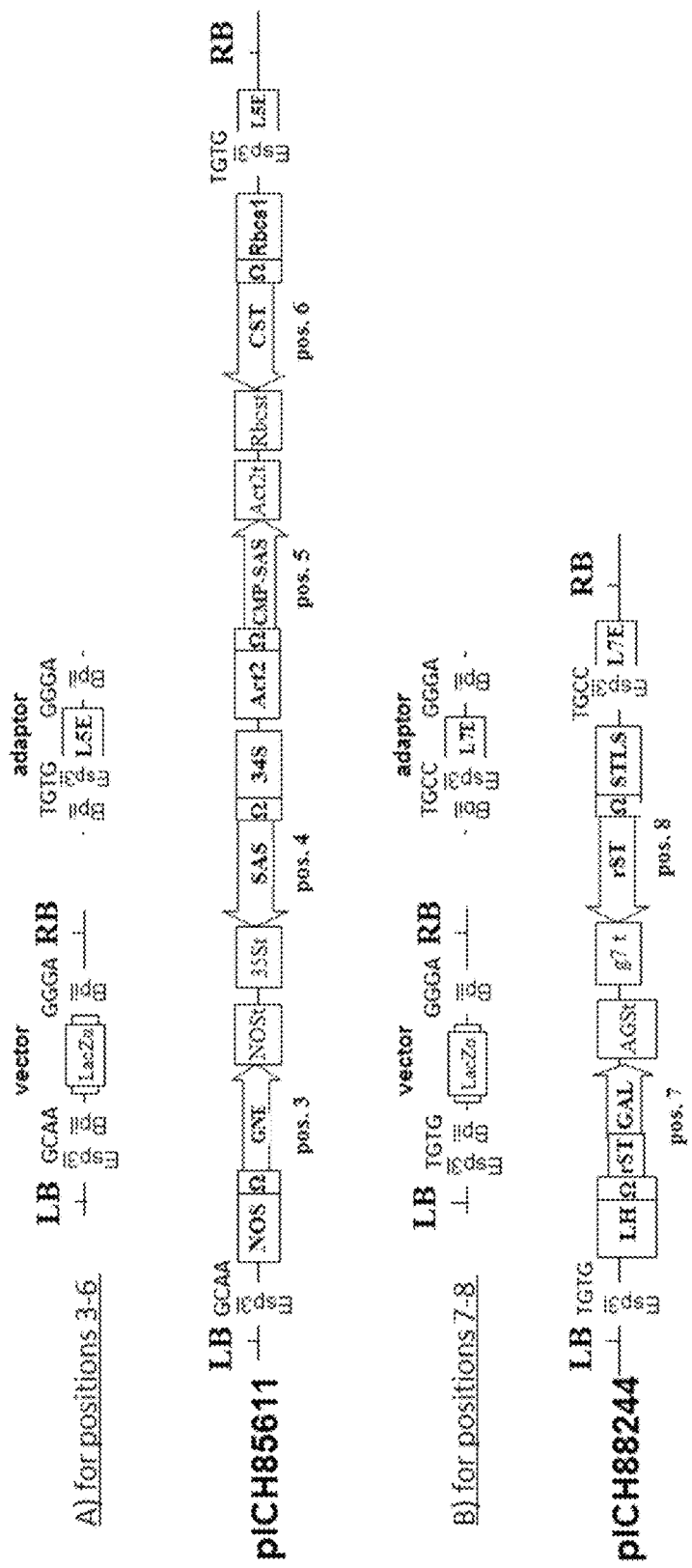
Figure 4B – Assembly of multigene construct pICH88266, Intermediate constructs assembled with BpiI (level M)

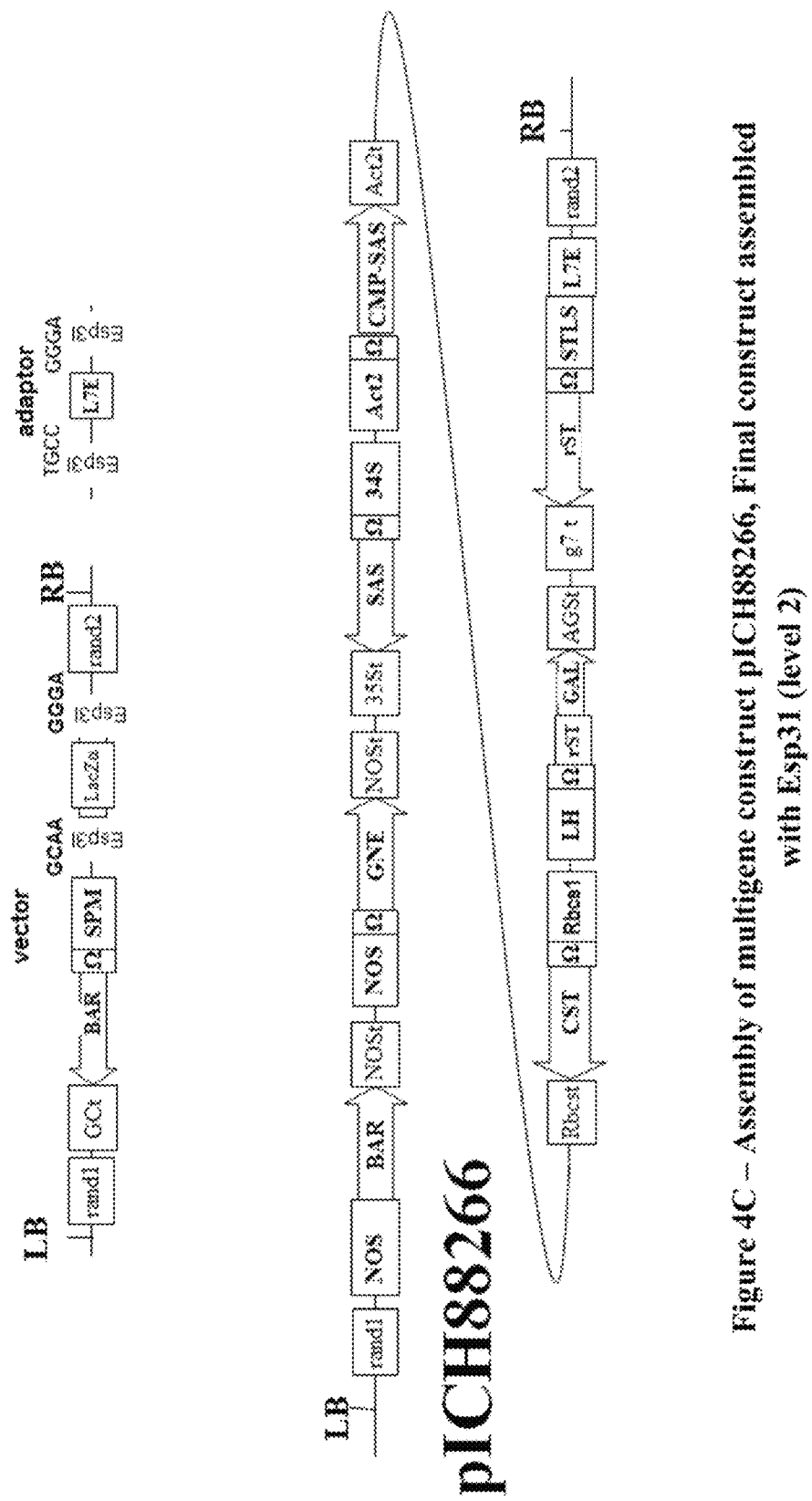
Figure 4C – Assembly of multigene construct pICH88266, Final construct assembled with Esp31 (level 2)

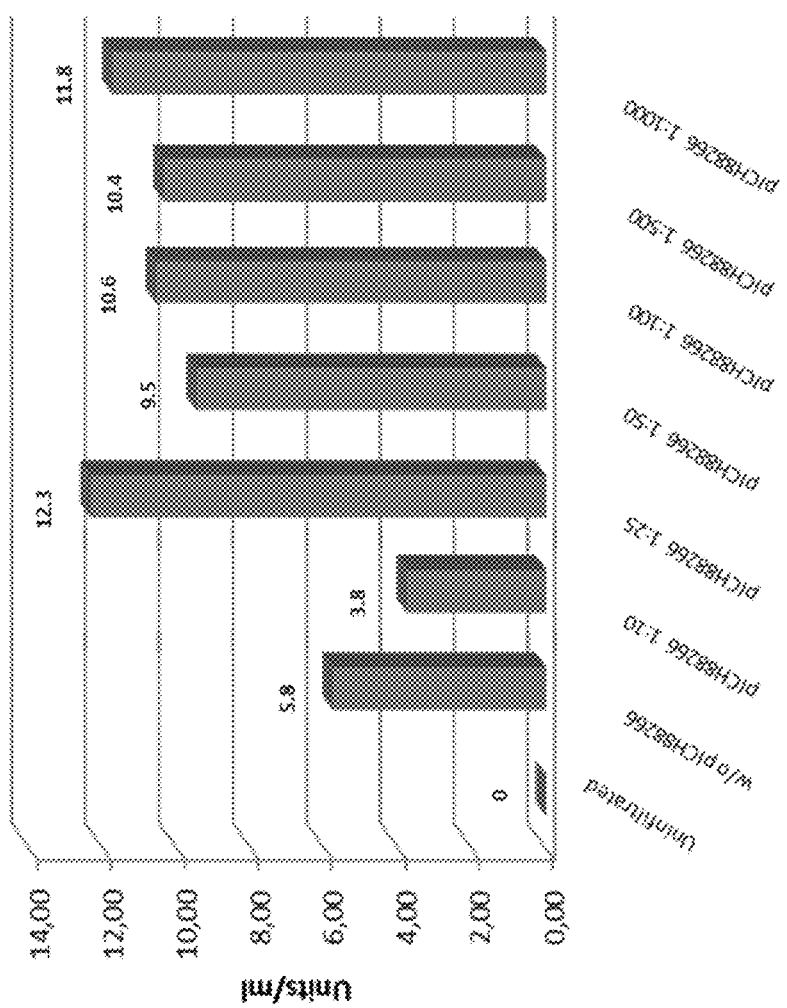
Figure 5 – BCHE activity in crude plant extracts

Lane 1 – Mark 12, 8.0μl (gel) or
BIORAD, 10.0μl (western)
Lane 2 – BCHE Standard, 5.0μl
Lane 3 – Empty
Lane 4 – BCHE tetramer transient sialyation Sample 1 (~150.0ng)
Lane 5 – BCHE tetramer transient sialyation Sample 2 (~150.0ng)
Lane 6 – BCHE monomeric transient sialylation. (~165.0ng)

| pICH88266 dilution | | 1:10 | 1:25 | 1:50 | 1:100 |
|---|---|---|---|---|---|
| Glycan | | % of total peak height | | | |
| GnGnXF | | 4.0 | 10.8 | 8.6 | 14.5 |
| MAXF | | 0 | 0 | 1.1 | 0 |
| GnAXF | | 0 | 0 | 0 | 0 |
| MNaXF | | 14.9 | 16.8 | 18.9 | 10.4 |
| AAXF | | 4.7 | 0 | 3.9 | 4.6 |
| GnNaXF | | 0 | 0 | 0 | 0 |
| ANaXF | | 15.2 | 16.0 | 15.9 | 15.0 |
| NaNaXF | | 16.1 | 16.1 | 22.1 | 16.1 |
| Man8 | | 18.7 | 18.1 | 13.1 | 17.8 |
| Man9 | | 26.4 | 22.2 | 13.7 | 18.7 |
| Man10 | | 0 | 0 | 2.7 | 2.9 |
| Total sialylated glycans (%) | | 46.2 | 49.0 | 56.9 | 41.5 |

Figure 19
| Dominant Glycan Structure/Site | (missing Asn134 Asn 284) | Asn17 (mature) Asn 45 | Asn57 (mature) Asn 85 | Asn256 (mature) Asn 269 | Asn341 (mature) Asn 369 | Asn455 (mature) Asn 383 |
|---|---|---|---|---|---|---|
| 2022 |  | 63.9% | 70.8% | 58.0% | 48.4% | 71.7% |
| 2021 |  | 2.1% | 2.0% | 2.7% | 2.8% | 2.6% |
| 2122 |  | 0.0% | 5.0% | 7.8% | 0.0% | 7.6% |
| Core |  | 14.0% | 6.9% | 10.8% | 6.8% | 11.2% |
| Agly |  | 0.0% | 0.5% | 13.8% | 27.6% | 0.6% |

Figure 20

| Nb RNAi Plant line T1 | Ratio of ppt-sensitive/resistant | Insertion site identified | Screening for homozygous lines | Propagation homozygous plants of T1 generation | Analysis of T2 generation |
|---|---|---|---|---|---|
| Nb88266-5 | 1.9:1 | Yes (single) | 6 (of 17) single T1-plants are potentially homozygous | 6 (of 6) homozygous plants: continuously collecting seeds in process | Homozygous T2-generation plants confirmed (ppt plates) <br><br> Growing of T2 generation plants for confirmation of sialylation ability by transient infiltration with rBCHE |
| Nb88266-11 | 2.7:1 | Yes (single) | 11 (of 22) single T1- plants are potentially homozygous | 11 (of 11) homozygous plants: continuously collecting seeds in process | Homozygous T2-generation plants confirmed (ppt plates) <br><br> Sialylation ability of T2-generation plants (6 of 6 lines) could be confirmed by transient infiltration with rBCHE |
| Nb88266-22 | 3.5:1 | Yes (single) | 8 (of 17) single T1-plants are potentially homozygous | 8 (of 8) homozygous plants growing → not yet flowering Sialyation ability of T1-generation plants (8 of 8 lines) confirmed by transient infiltration with rBCHE. Unexpectedly, these plants might die due to infiltration (→ restart with screening for homozygous plants required) | |

Figure 21

| Plant line | Plant No | Homozygosity confirmed in T2 generation plants | Sialylation ability confirmed on T2-generation plants | Seeds of | Amount seeds harvested [gram] | Seeds ready for shipment to KBP [gram] |
|---|---|---|---|---|---|---|
| Nb88266-11 | 2 | Yes | Yes | T1 generation | 1,9 | 1,0 |
| Nb88266-11 | 3 | Yes | Yes | T1 generation | 1,7 | 1,0 |
| Nb88266-11 | 9 | Yes | Yes | T1 generation | 1,6 | 1,0 |
| Nb88266-11 | 13 | Yes | not yet tested | T1 generation | 0,7 | 0,5 |
| Nb88266-11 | 15 | Yes | Yes | T1 generation | 0,8 | 0,5 |
| Nb88266-11 | 16 | Yes | Yes | T1 generation | 0,9 | 0,5 |
| Nb88266-11 | 20 | Yes | Yes | T1 generation | 1,0 | 0,5 |
| Nb88266-11 | 24 | Yes | not yet tested | T1 generation | 0,9 | 0,5 |
| Nb88266-11 | 26 | Yes | not yet tested | T1 generation | 1,0 | 0,5 |
| Nb88266-11 | 29 | Yes | not yet tested | T1 generation | 0,7 | 0,5 |
| Nb88266-11 | 30 | Yes | not yet tested | T1 generation | 1,2 | 1,0 |

Figure 22

| Plant line | Plant no. | Sialylation ability confirmed on T2-generation plants |
|---|---|---|
| Nb88266-11 | 2 | Yes |
| Nb88266-11 | 3 | Yes |
| Nb88266-11 | 9 | Yes |
| Nb88266-11 | 13 | not yet tested |
| Nb88266-11 | 15 | Yes |
| Nb88266-11 | 16 | Yes |
| Nb88266-11 | 20 | Yes |
| Nb88266-11 | 24 | not yet tested |
| Nb88266-11 | 26 | not yet tested |
| Nb88266-11 | 29 | not yet tested |
| Nb88266-11 | 30 | not yet tested |

Figure 23

| Theoretical m/z | Observed m/s | Proposed Assignment | Structure | MS/MS |
|---|---|---|---|---|
| 1579.7826 | 1579.80 | (GlcNAc)2(Man)5 | 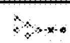 | Loss reducing end HexNAc, Loss terminal Hex |
| 1620.8091 | 1620.82 821.91 (z=2) | (GlcNAc)3(Man)3(Gal) | 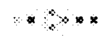 | Loss reducing end HexNAc, Loss terminal Hex+HexNAc |
| 1736.8565 | 1736.87 879.93 (z=2) | TRUNCATED (GlcNAc)2(Man)3(Gal)(NeuAc) | 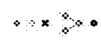 | Loss terminal NeuAc, loss internal Hex+HexNAc |
| 1783.8824 | 1783.90 903.44 (z=2) | (GlcNAc)2(Man)6 | 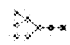 | Loss reducing end HexNAc, Loss terminal Hex |
| 1824.9089 | 1824.93 923.96 (z=2) | (GlcNAc)3(Man)5 AND TRUNCATED (GlcNAc)3(Man)3(Gal)2 |  | Loss reducing end HexNAc, Loss terminal HexNAc, Loss terminal HexNAc+Hex |
| 1981.9828 | 1982.00 1002.49 (z=2) | (GlcNAc)3(Man)3(Gal)(NeuAc) | 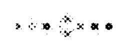 | Loss reducing end HexNAc, Loss terminal NeuAc, Loss internal HexNAc+Hex |
| 1987.9821 | 1988.98 1005.49 (z=2) | (GlcNAc)2(Man)7 | 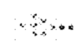 | Loss reducing end HexNAc, Loss terminal Hex |
| 2070.0352 | 1046.52 (z=2) | (GlcNAc)4(Man)3(Gal)2 | 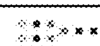 | Loss terminal HexNAc+Hex (2X) |
| 2186.0826 | 1105.05 (z=2) | TRUNCATED (GlcNAc)3(Man)3(Gal)2(NeuAc) | 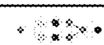 | Loss terminal NeuAc Loss internal HexNAc+Hex |
| 2192.0819 | 1107.55 (z=2) | (GlcNAc)2(Man)8 | 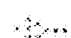 | Loss reducing end HexNAc, Loss terminal Hex |
| 2227.1091 | 1125.56 (z=2) | (GlcNAc)4(Man)3(Gal)(NeuAc) | 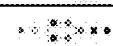 | Loss terminal NeuAc Loss internal HexNAc+Hex. |
| 2390.1824 | 1206.60 (z=2) | (GlcNAc)3(Man)5(Gal)(NeuAc) | 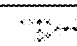 | Loss terminal NeuAc, Loss reducing end HexNAc |
| 2396.1817 | 1209.60 (z=2) | (GlcNAc)2(Man)9 | 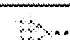 | Loss reducing end HexNAc, Loss terminal Hex |
| 2431.2089 | 825.74 (z=3) 1227.11 (z=2) | (GlcNAc)4(Man)3(Gal)2(NeuAc) | 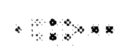 | Loss terminal NeuAc Loss internal HexNAc+Hex, Loss reducing end HexNAc |
| 2547.2563 | 864.75 (z=3) 1285.14 (z=2) | TRUNCATED (GlcNAc)3(Man)3(Gal)2(NeuAc)2 | 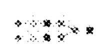 | Loss terminal NeuAc (2X) Loss internal HexNAc+Hex, (2X) |
| 2792.3826 | 946.13 (z=3) 1407.70 (z=2) | (GlcNAc)4(Man)3(Gal)2(NeuAc)2 | 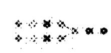 | Loss terminal NeuAc(2X), Loss reducing end HexNAc |

PLANT-BASED RECOMBINANT BUTYRYLCHOLINESTERASE PRODUCTION METHODS

CROSS-REFERENCE TO RELATED APPLICATIONS

This divisional patent application claims priority to and benefit from, currently pending, U.S. patent application Ser. No. 14/448,545, filed on Jul. 31, 2014, which claims priority from U.S. Provisional Patent Application No. 61/885,492, filed on Oct. 1, 2013, which are hereby incorporated by reference.

STATEMENT OF GOVERNMENT RIGHTS

The invention was made with Government support under contract No. HR0011-12-C-0103 awarded by the Defense Advanced Research Projects Agency (DARPA) of the United States with technical representation under the contract by the United States Army Research Office. The Government has certain rights in the invention.

REFERENCE TO A SEQUENCE LISTING

This application contains a Sequence Listing in compliance with 37 C.F.R. § 1.52(e) that is hereby incorporated by reference in its entirety. The sequence listing text file submitted via EFS contains the file "Divisional Sequence Listing ST25.txt" as a computer readable form, was created on Jun. 26, 2017, and is 3332 bytes in size.

FIELD OF THE INVENTION

A new, reliable, easily scalable and reproducible method for the production of recombinant butyrylcholinesterase (rBuChE) is provided. Through the utilization of a plant transfection procedure, various plant strains have been shown to generate effective and scalable amounts of rBuChE under acceptable manufacturing processes to permit reliable levels of such enzymes for desired nerve agent protection requirements (including tetrameric products). As well, such methods in engineered plant lines have shown suitable production of these enzymes in tetramer form with glycan formation and sialylation (for terminal groups) to allow for optimal potency against organophosphorus agent exposure as well as proper immunogenic response within the plant sources. The overall production method, including the transfection and production within live cells (whether fungi, bacterial, plant, or animal cells), as well as the process steps involved for such a reliable sourcing platform from plants is thus encompassed within the invention.

BACKGROUND OF THE INVENTION

Organophosphorous compounds (OPs) act as potent inhibitors of acetylcholine-hydrolyzing enzymes. Their ability to inhibit acetylcholinesterase, the primary synaptic regulator of cholinergic transmission, can result in highly toxic effects to humans ranging from irreversible neurological damage to death. OPs can be found in several forms, including relatively benign insecticides and far more troublesome weaponized chemical agents. Prior to World War II and extending into present times, various forms of OPs have been developed and deployed as nerve agents for nefarious purposes. These agents are classified into two general groups: 1) G agents, including Tabun (GA), Sarin (GB), Soman (GD) and Cyclosarin (GF); and 2) V agent, VX. G agents are generally non-persistent, volatile liquids in contrast with the highly persistent, non-volatile and more active VX compound. In spite of broad agreement to ban and destroy these chemical weapons, the relative ease of their synthesis and deployment makes these agents ideal tools for terrorist activities bringing about high risk to both civilian and military populations. Deployment of these agents poises an immediate health risk through respiratory or skin exposure as well as a latent threat through persistent residues on solid surfaces requiring extensive operational decontamination before reuse.

As an example, the release of sarin gas in the Tokyo subway system in 1995 provides an unfortunate illustration of the vulnerability of large population centers to chemical weapons of mass destruction (WMDs) and their potentially devastating effects. Within such a confined location, many individuals perished upon exposure to such an OPs agent. With such possible threats looming around the world (the current situation in Syria is yet another incidence), there exists the urgent need for strategies to address both human health risks as well as operational decontamination.

Acute exposure to organophosphate nerve agents is typically treated through repeated dosing of a cocktail of atropine, oxime reactivators (including 2-pyridine aldoxime methyl chloride, or 2-PAM) and anti-convulsants. These treatments suffer from significant adverse reactions, difficult compliance, and inadequate efficacy. New strategies to improve the performance of current drugs, reduce their dosage, or increase efficacy through added modes of action are required. Butyrylcholinesterase (BuChE) is a major serum human cholinesterase that shows remarkable promiscuity with regards to the chemical substrates that it binds and hydrolyzes. This property allows it to readily bind environmentally occurring OPs (pesticides) as well as both G and V classes of chemical nerve agents. In spite of a high binding constant (Km) to these diverse chemical agents, the hydrolysis (Kcat) is very slow leading to a functional inhibition stoichiometry of I enzyme:I OP molecule. Many groups have diligently sought to identify enzymatically active agents of both human and bacterial origin. As such, investigations have focused greatly on BuChE developments.

There are other conditions and situations within mammalian subjects, at least, wherein BuChE has proven to be of significance. For instance, it has been realized that certain neurological conditions, such as Alzheimer's, have shown a reliance upon butyrylcholinesterase for proper function and reduction in possible neural degradation. Likewise, certain physiological conditions caused by addictive substances, cocaine, for example, may be treated through the introduction of BuChE as a treatment. There are also enzyme replacement therapies including the utilization of introduced butyrylcholinesterase to overcome subject deficiencies in natural amounts present within a body or even through the presence of mutated BuChE enzymes genes that cause reduced amounts to be generated within a subject organism. In essence, even though the potential for OPs intoxication treatments are of significance in the utilization of BuChE of any type, there exist other situations wherein a need for effective BuChE production can be of great benefit, as well.

Early studies demonstrated that hBuChE purified from the sera of equine and human sources could protect mice, guinea pigs and non-human primates from 3-5 $LD_{50}$ doses of various OP nerve agents of both classes. The human serum derived BuChE shows tetrameric nature and glycan structures terminated with sialic acid leading to about a 73 hour half-life in the serum of experimental animals, thereby providing an enzyme that has been shown to be safe in human clinical trials. However, the requirement of 200 mg of the enzyme to treat a dose of 2-5 $LD_{50}$ of soman (in an average sized human) renders sera sourcing unfeasible due to volumes of source material available and low yields. Recombinant BuChE (rBuChE) has been produced from transgenic goats but shows primarily monomer or dimer structure, little sialic acid termini and a rapid half-life in serum. Modification with polyethylene glycol is required to achieve a favorable pharmacokinetic profile, and has yet to be properly tested for human safety through clinical trials. Additionally, both sources of BuChE, expired human plasma or transgenic goats, appear inadequate in amount and too high in cost to provide the needed amounts of BuChE for at-risk military and civilian populations.

Because of the promise of potency, specificity, and safety profile, rBuChE is an appealing platform for OP protection. However, addressing the challenges of weapons of mass destruction (WMD) with enzymatic products presents several unique manufacturing challenges. Scale is important to address the various applications related to WMD protection and response. Modest level production can be used to provide both preventative and post-exposure responses for military populations in at-risk areas. Extremely high levels of production will be necessary to insure adequate supplies of product to address civilian exposure in the case of WMD release, as well. Typical production methods for monoclonal antibodies (mAbs) use mammalian cell reactors. Whereas this approach has been successfully used to address diseases with predictable supply requirements, large-scale mammalian culture is not well suited for rapid response and varying scale production due to capital requirements associated with cell growth facilities. Space and use amortization does not provide a conducive incentive for the enormous costs (e.g., in excess of $500M, from some estimates) required to build a suitable upstream facility. Additionally, the timeframes for needed product turnaround cycles are generally inadequate for continuous supply options. Furthermore, as new enzymatic products become available to address broader chemical structures and specificities, the process from construct development to cGMP production can reach 2-3 years in duration due to cell line optimization, process adaptation and requisite scale-up requirements (particularly in terms of mammalian-based production sources)(not to mention the general costs with husbandry, sanitation, feeding, etc., for such animals, including new generations thereof). Finally, traditionally manufactured mAbs (e.g. CHO or NS0 cells) have insufficient sialylation and other glycan modification capabilities to potently provide a long-lasting protective and therapeutic product necessary for the unpredictability of nerve agent exposure. Mammalian cell lines that offer minimal sialylation or chemical sialylation methods are unpredictable and are, among other things, subject to high royalty rates stacking onto the already significant production costs. Such escalated cost structures thus disfavor their consideration as a solution for WMD challenges. These limitations indicate a distinct desire for a new, more scalable, responsive and efficacious production strategy for such an enzyme product.

Of further importance is that previous work on BuChE structures could not provide a tetramer formation coupled with sialylation results. In particularly, it was determined that sialylation of cells could be accomplished for recombinant butyrylcholinesterase products, but the ability to provide tetramers thereof were impossible, particularly within mammalian cell bases. Thus, even though a butyrylcholinesterase platform is quite attractive for a number of treatment purposes, particularly within mammalian systems, the ability to produce not only cost-effective products in this manner, but also such products that exhibit suitable compatibility for mammalian treatments (e.g., sialylated and tetramerized), have yet to be developed. To date, in essence, there simply have not been any effective developments that provide reliable sources of BuChE with sialylated tetramer formations through repeatable processes and at low overall costs in comparison.

Advantages and Summary of the Invention

It has now been determined that plant-based systems offer a distinct advantage over solely mammalian production schemes and manufacturing problems due to its overall speed and scalability benefits, as well as the uniformity of tetramerized structures exhibiting highly desirable sialylation and glycan formations. Through the use of engineered plant organisms, including, without limitation, *Nicotiana benthamiana* (Nb) strains, such plant-produced enzymes allow for the provision of a suitable amount and source for a lead vaccine candidate from expression construct within a desired time period. Such a system also provides the distinct advantage of highly homogenous glycans in common with mammalian systems, including sialic acid that lack significant levels of plant-specific glycan linkages, which eliminate any safety concerns about plant-specific immunogenicity when utilized within a therapeutic, vaccine or other type of human delivery process. Plant-based systems offer yet another advantage over mammalian types through significant cost savings (in both costs for construction of a manufacturing facility as well as COGS manufactured) compared to traditional mammalian cell culture manufacturing. Such a method described herein provides the advantageous capability of reliable tetramer formation and sialylation of BuChE within other types of living cells, as well, including, without limitation, eukaryotic microbial cells, such as yeast, *Saccharomycetes*, and *Pichia*, as well as other animal cells, including mammalian cells.

Plants have steadily gained regulatory acceptance as alternative production systems for biologics. The present inventive approach produces rBuChE using a plant platform with rapid production surge capability and can be used to rapidly address challenges associated with differential product requirements and adapted to address threats against novel and re-emerging pathogens. The overall procedure includes the utilization of a transient plant-based production approach allowing agricultural scaling of upstream biomass and raw product with traditional downstream protein purification, release, and formulation. Through this approach, the plant-based system offers significant advantages in scale, cost and flexibility compared with traditional mammalian manufacturing.

The rBuChE product generated through one potential embodiment described herein is produced through a transient plant expression system exhibiting surge capability and useful to rapidly address the unpredictability of timing and scale of nerve agent threats in civilian and military settings. Via the use of engineered plant varieties, including, as one non-limiting example, *Nicotiana* strains, plant-produced rBuChE products have, as noted above, highly homogenous mammalian-like glycans lacking significant levels of plant-specific linkages, eliminating any safety concerns about plant-specific immunogenicity. It has also been discovered that plant-derived enzymes are equivalently potent as those produced by traditionally manufactured mAbs (e.g. CHO, Per-C6 or NS0 cells) including alpha galactosidase A, lysosomal acid lipase and rBuChE. In addition to potency benefits, the plant-based system allows rapid scalable production of novel enzymes showing increased potency or specificity (e.g. against a new chemical agent). A manufactured lot of a new enzyme with appropriately engineered glycans could be produced and released in one month with a time to cGMP production of approximately 6 months (which is 2-3 times quicker than via mammalian cell culture). The inventive plant-based production system also offers significant cost-savings (both with respect to costs for construction of a manufacturing facility and cost of goods manufactured) compared with traditional mammalian cell culture manufacturing.

Accordingly, this invention encompasses a recombinant butyrylcholinesterase product exhibiting at least about 50% sialylation and at least about 50% tetramer formation (that may be produced from plants, plant cells, and other live cells, including eukaryotic microbial cells, such as yeast, Saccharomycetes, and Pichia, as well as other animal cells, including mammalian cells), and preferably exhibiting at least 70% sialylation and at least 60% tetramer formation. Also encompassed herein is a method for production of recombinant butyrycholinesterase from a plant, a plant cell, or both (or any living cell, whether plant or animal, alternatively), said method comprising the following steps: a) providing said plant, plant cell, or both (or other living cell), with at least one vector capable of expressing said butyrylcholinesterase; b) incubating said plant, plant cell, or both (or living cell), at conditions that cause the synthesis of said butyrylcholinesterase and including the generation of sialylated glycans, tetramer formation, or both, on said butyrylcholinesterase to form a butyrylcholinesterase product exhibiting at least one of sialylation and tetramer formation; and c) isolating said butyrylcholinesterase product of step "b" from said plant, plant cell, or both (or living cell) (preferably where the product exhibits both sialylation and tetramer formation, such as at least about 50% sialylation, more preferably at least 70%, and at least about 50% tetramer formation, more preferably at least 60%). Furthermore, the production method wherein said conditions that cause the generation of sialylated glycans on said butyrylcholinesterase include the introduction within said living cell of genes expressing at least one of sialic acid synthesis, galactose transfer, and sialic acid transfer, wherein said gene expressions generate butyrylcholinesterase sialylation in vivo, or, alternatively or simultaneously, wherein said conditions that cause the generation of tetramer formation on said butyrylcholinesterase include the introduction within said living cell of genes endogenous to said living cell and expressing at least one of sialic acid synthesis, galactose transfer, and sialic acid transfer, wherein said gene expressions generate butyrylcholinesterase sialylated tetramers in vivo, is also encompassed herein. Additionally, this invention further encompasses such a method wherein said at least one vector of step "a" (from the method outlined above) expresses peptide tetramerization and also expresses glycoprotein sialylation. The overall invention also encompasses a method of treating a mammalian subject, said treatment including the steps of: a) providing a recombinant butyrylcholinesterase product exhibiting at least about 50% sialylation and at least about 50% tetramer formation; b) introducing said product of step "a" within a suitable composition or formulation for internal transfer within a mammalian subject; and c) introducing said recombinant butyrylcholinesterase-containing composition or formulation of step "b" into said mammalian subject through an intravenous or intramuscular procedure, for the purpose of, as one example, reducing or preventing organophosphorus agent intoxication.

Utilizing a plant-based transient expression platform in relation to this invention, again, as one example, an Nb platform, rBuChE has not only been produced in full tetramer conformation at a resultant purity in excess of 99% retaining expected specific activity and nerve agent binding properties, but such results have been passed on to plant generations through genetic modifications within seeds. Thus, the generation of such rBuChE production schemes has been provided in a reproducible and scalable form that is cost-effective and reliable. Additionally, a transient sialylation system was developed to provide the requisite post-translational modifications in this respect, as well. As noted above, such sialylation and tetramerization results are of significance for supplying the industry with effective means to combat organophosphorous-based agents. In comparisons, the monomer/dimer rBuChE neat (non-sialylated product) showed a serum half-life of about 30 minutes, while the sialylated monomer/dimer showed a half-life of roughly 4 hours. The tetramer/sialylated product of the current invention, however, particularly with a nearly 50% occupancy of terminal sialic acid present, showed a serum half-life of about 44 hours. An increase in sialic acid occupancy (such as greater than 70% with terminal sialic acid residues through modification of the glycosylation pathway in the production host) exhibits a terminal pharmacokinetic half-life of more than 63 hours when delivered intravenously and in excess of 86 hours when delivered through the intramuscular route, using control enzyme activity as baseline as shown in Table 1, below. It appears evident, then, that there exists a minimally additive, and possibly synergistic, role for tetramerization and sialylation to increase the rBuChE PK half-life. These half-life values are significantly higher than any other recombinant form of rBuChE reported to date.

Such results signify that the capabilities available with plant-based production schemes were more than adequate in terms of PK properties, at least, for human delivery intravenously or intramuscularly. Table 1, below, shows comparative considerations in this respect and the unexpectedly effective results for the inventive plant-based systems versus other production procedures of similar structures.

TABLE 1

Comparison of BuChE pharmacokinetic half-life results using background enzymatic activity as baseline

| Source | Pharmacokinetic Results T½ |
|---|---|
| Native serum-derived hBuChE (~99% Tetramer) with ~80% sialic acid Occupancy[1] | 72 hours (GP) 56.6 hours (mice) |
| Chinese Hamster Ovary (CHO) produced Monomer[1] | 2 min (mice) |
| CHO produced tetramer (70% tetramer)[1] | 16 hours (mice) |
| CHO produced tetramer (70% tetramer) plus Chemical sialylation[2] | ~17 hours (mice) |
| Goat produced rBuChE (dimer)[3] | 7.3 hours (GP) |
| Goat produced rBuChE-hSA fusion (tetramer)[4] | 32 hours (GP) |
| *Nicotiana* produced rBuChE tetramer (75%), 99% purity with transient sialylation (69% Occupancy) | 63.4 hours (GP) IV 86.4 hours (GP) IM |

[1]DARPA/USAMRICD data; *J. Pharmacol. Exp. Ther.* 302, 751-758
[2]*PNAS* Jan. 22, 2013, vol. 110 no. 4 1243-1248
[3]*Proc. Natl Acad. Sci. U.S.A.* 2007, Aug., 21; 104(34): 13603-8
[4]*BMC Biotechnology* 2008, 8: 50

Thus, the plant-based recombinant product with tetramer formation and high sialic acid occupancy is clearly an attractive candidate for in vivo protection against nerve agent exposure due to high levels of enzymatic and agent affinity as well as pharmacokinetic properties.

It was thereby realized that improvements in actual production methodologies would be important to make this possible pathway viable. To that end, it was determined that, in order to further reduce costs and strengthen production possibilities of the tetramer sialylated rBuChE product, a set of transgenic plant lines were derived that showed the ability to produce tetramer sialylated rBuChE through multiple generations. The potential to optimization such plant lines, including production using transgenic hosts, derivation of later generation seed, and individual testing for sialylation capabilities of individual lines creates further attractiveness for this overall method. For instance, through analysis of four transgenic production rBuChE batches, three showed 70-73% terminal sialic acid occupancy, and another showed about 50%. Such measured levels were similar to those observed with transient samples. Transgenic production shows results wherein levels of sialylation developed from seeds of engineered plants exhibit differing occupancy measurements, but at levels that are acceptable, generally, for effective intravenous and intramuscular delivery purposes. Individual plants, referred to herein as the T3 lines, appear to function in similar ways, as well. In effect, without relying upon any specific scientific basis, it has been realized that plants offer a rapid, surge compatible approach to produce a superior recombinant form of tetramerized, sialylated rBuChE, which shows attractive PK properties. These resultant rBuChE structures produced in accordance with the invention were also tested for viability within mammalian organisms (Hartley Guinea Pigs)(through intravenous and intramuscular introductions, as noted above). The results were as follows show a t½ of 63.4 hours when delivered via an intravenous (IV) route and at least 86 hours when delivered via an intramuscular (IM) route. The accompanying data is further detailed in Table 2.

Initial efficacy testing was also undertaken in the same Hartley Guinea Pig population to assess the viability of transiently sialylated rBuChE product in nerve agent tests. Such tests encompassed utilization of the rBuChE products used within the SRI Definitive Pharmacokinetic studies, above, and tested for short time dosing efficacy using intravenous delivery of rBuChE. The plant-produced rBuChE showed efficacy against GD, GB and VX in guinea pig models demonstrating translation readiness of the product.

Tests were initially undertaken for GD and VX Nerve Agents that administration of inventive plant-based tetramer sialylated BuChE to male Hartley guinea pigs (300-350 grams) via an IV carotid catheter at 26.15 mg/kg. After 15 minutes, animals administered 26.15 mg/kg were exposed to 3×LD50 of GD or VX via s.c. injection (n=6 for each).

For GB Nerve Agent, the subject guinea pigs were administered inventive plant-based tetramer sialylated BuChE to male Hartley guinea pigs (300-350 grams) via an IV carotid catheter at 52.3 mg/kg. After 15 minutes, the subject animals were then exposed to 3×LD50 of GB via s.c. injection (n=6). In each sample, all animals survived to 24 hours with no signs of OPs intoxication. Due to similar levels of tetramerization and sialylation of rBuChE produced using transgenic plants capable of sialyating proteins compared with the transient sialylation methodology used to produce the materials tested in guinea pigs, similar efficacy results for transgenically derived products were postulated.

These data show this methodology produces efficient tetramer product (having greater than 60% tetramer formation) and highly sialylated product (having greater than 50% sialylation) from total isolation of rBuChE rather than selective isolation of product to show measurable sialylation (Schneider et al., 2014. Plant Biotechnol. J. March 11. doi: 10.11 11/pbi.12184[16]; Schneider et al Biotechnol J. 2014 April; 9(4):501-10[17]). In these articles, only rBuChe derived from the interstitial fraction (apoplast) from transfected leaves show greater than 40% sialylation. Further, the prior work in this area has shown repeatedly production methods that result in very low expression of rBuChE such that no purified materials were analyzed by SDS-PAGE gels and directly visualized by Coomassie Blue or other staining agents. Such prior work does not present data demonstrating oligomerization, in particular the formation of stable tetram-

TABLE 2

Summary Data from SRI Definitive Pharmacokinetic Study in Hartley Guinea Pigs

| Guinea Pig | $C_{max}$ (U/ml) | $T_{max}$ (hr) | $t_{1/2}$ (hr) | $AUC_{last}$ (hr · U/ml) | Cl (ml/hr/kg) | Vss (ml/kg) | $MRT_{inf}$ (hr) | F (%)** |
|---|---|---|---|---|---|---|---|---|
| Intravenous group, 25 mg/kg (13125 U/kg) | | | | | | | | |
| 1 | 60.7 | Not applicable (NA) | 61.3 | 977.0 | 11.6 | 877.0 | 75.3 | |
| 2 | 68.0 | NA | 64.2 | 1178.0 | 9.3 | 778.0 | 83.5 | |
| 3 | 62.5 | NA | 64.7 | 1086.0 | 9.7 | 901.0 | 92.5 | |
| 4 | 62.7 | NA | 74.0 | 1239.0 | 8.4 | 820.0 | 97.9 | |
| Mean | 63.5 | | 63.4 | 1120.0 | 9.8 | 844.0 | 83.8 | |
| SD | 3.1 | | 1.8 | 114.0 | 1.3 | 56.0 | 8.6 | |
| Intramuscular group, 25 mg/kg (13125 U/kg) | | | | | | | | |
| 5 | 7.7 | 36.0 | 82.5 | 694.0 | Not calculated (NC) | NC | 135.9 | 62 |
| 6 | 7.4 | 36.0 | 89.9 | 671.0 | NC | NC | 151.0 | 59.9 |
| 7 | 7.5 | 36.0 | 86.9 | 712.0 | NC | NC | 138.4 | 63.6 |
| 8 | 8.0 | 36.1 | 77.0 | 681.0 | NC | NC | 129.2 | 60.8 |
| Mean | 7.7 | 36.0 | 86.4 | 86.4 | 690.0 | | 141.8 | 61.8 |
| SD | 0.3 | 0.1 | 3.7 | 3.7 | 18.0 | | 8.1 | 1.9 |

**Calculated using $AUC_{last}$ values ers. The poor overall yields of the protein coupled with asymmetrically sialylated product localized in the ER and in the apoplast result in extremely low levels of produced tetramer and sialylated products overall. Low efficiency levels coupled with the difficulties inherent in purifying sialylated rBuChE material to homogeneous levels contribute to the lack of definitive measures of PK properties for this protein as well as the lack of any PK analysis involving such materials. Additionally, although transgenic expression of rBuChE has been found to result in about 50% tetramer formation, the resultant t½ measurements for such products were very low (about 4 min), particularly in native plant-produced forms (Geyer et al., PNAS, Nov. 23, 2010, vol. 107, no. 47, 20251-20256[11]). To increase levels to achieve significant and biologically relevant PK properties, conjugation of the enzyme with PEG (5 k or 20 k) has been undertaken. Indeed, PEG-rBuChE conjugates show 3-5 hour initial clearance t½ and 23-58 hour t½ (5 k PEG) and about 15 hour t½ (20 k PEG) for second slow clearance phase value of a biphasic PK plot. The transient method disclosed herein, to the contrary, provides a manner to significantly improve tetrameric formation of rBuChE in plants compared with the transgenic method of Geyer et al., as well as produces an in vivo sialylated product with improved PK properties compared with the PEG-modified transgenic plant product (63.4 hours IV and 86 hours IM of sialylated tetramer plant product compared with a maximum of 58 hours IV for PEG modified transgenic product, particularly in comparison with the second clearance phase for the PEG product). Further, the transgenic methodology shows inefficient yields and at very low product accumulation (basically, in amounts that are inappropriate from an economic perspective, such as discussed within Geyer et al.; Castilho et al., 2008[1]; Castilho et al., 2010[2]; Castilho et al., 2011[3]; and Castilho et al., 2011[4]). Additionally, Ilyushina et al., www.pnas.org/cgi/doi/10.1073/pnas.1211118110[14]) show tetramer accumulation of up to 70% from transfected mammalian cells. The t½ of the mammalian produced enzyme is measured asabout 15-16 hours in rats and mice, respectively, when native mammalian glycosylation (lacking sialylation) is present (Duysen et al., 2002). Ilyushina et al. disclose an in vitro polysialyation method within mammalian cells to produce and purify rBuChE tetramers. This ex-vivo sialylation methodology, however, has been less efficient, more expensive, and less attractive in terms of pharmacokinetic profile than the present method of producing in vivo sialylated tetramer proteins from plants. Natively produced rBuChE from CHO (Chinese hamster ovary) cells shows a t½ of 3-4 hours in mice. In vitro sialylation improves the PK profile to between 16-23 hours. These times are, however, about 3 times less than that observed the plant-produced in vivo sialylated rBuChE tetramers disclosed herein. These data show the superiorities of the transient plant expression method to produce sialylated tetrameric rBuChE. Furthermore, as discussed in greater detail below, transgenic sialylation of transiently expressed rBuChE produces comparable sialylation and tetramerization efficiency as transient approaches, particularly in terms of economies of scale and production.

Of further consideration, there exists a proprietary mammalian cell line PerC6 that has exhibited a capability to sialylate human proteins (Diaz et al., 2009[5]). However, such work has not extended to the level of suggestion that would allow for the combination of tetramerizing peptides with PerC6 sialylation. For instance, U.S. Pat. No. 8,729,245, to Yim et al.[6], describes the difficulties involved in producing a tetramer rBuChE in large part due to the tetramer size. Also, mammalian cell-produced rBuChE, with or without tetramerizing peptides present, are mixtures of tetramer, dimer and monomer forms at very low yields. The manufacturing process itself is very complex, the resultant half-life is very short (requiring pegylation for stability), the resultant product is highly heterogeneous in overall structure (and rather difficult to characterize and gain FDA approval, as a result), and comes with very high production costs. As a result, this Yim et al. disclosure centers on truncated monomeric forms of rBuChE, and not tetrameric sialylated structures. Such a path has been typical within this industry, ostensibly due to the difficulties present in terms of yields, costs, and final product properties. The Yim et al. work was thus limited to the production of a monomer sialylated rBuChE in PerC6 cells.

Additionally, such a disclosure was limited to biochemical characterizations of such products and not in terms of actual pharmacokinetic behavior. The present invention described herein demonstrates that monomer/dimer sialylated products show much less stability in living animals (Tables 1-2; 16-17). Additionally, the Yim et al. contention that the dimer/tetramer sialylated product stability issues exist due to the lack of proper glycosylation and/or sialylation is shown below to be inaccurate (Table 16, below). Therefore, the methods described herein demonstrate a method unknown to the art to produce high yielding sialylated, tetramer forms of rBuChE with similar pharmacokinetic activities as native human BChE.

Thus, in terms of base products generated through the inventive plant-based procedures show great promise for OPs protections. Further studies pertaining to the degree and type of sialylation on the tetramerized structures, including mono- and oligo-saccharide identification and profiling were followed as well. Additionally, the ability to, as alluded to above, provide plant lines for continuous and scalable product manufacturing purposes was investigated for overall reliability concerns, and the further capacity to readily produce the necessary tetramerized form, were also undertaken to show viability of the inventive methods for such purposes. Furthermore, the capability for glycan formation on such tetramerized forms has been shown to be a scalable and repeatable process. Lastly, the ability for seed lines to be generated in this manner for readily available and reliable production means was proven. This plant-derived method for producing rBuChE is also a cost-effective manner. In essence, leveraging economies of scale using plant-based systems and optimization of the manufacturing process, allows for commercial scalability without compromising effectiveness of the final products. Such overall production capacity and effective treatment results are shown in greater detail below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 provides a presentation of the plant transfection procedure of the overall rBuChE production system.

FIG. 2 provides a representation of the "At scale" transfection procedure of FIG. 1.

FIG. 3 provides a representation of samples of monomeric rBuChE produced by the inventive method.

FIG. 4A is a schematic presentation of level 1 expression cassettes for assembly of multigene construct of the pICH88266 providing for sialylation pathway of the inventive production method.

FIG. 4B is a schematic presentation of level M intermediate constructs for assembly of multigene construct pICH88266 providing for sialylation pathway.

FIG. 4C is a schematic presentation of final construct pICH88266 providing for sialylation pathway.

FIG. 5 depicts the measurement of the inventive butyrylcholinesterase (rBuChE) activity in crude plant extracts after co-infiltration of transient vector carrying BuChE gene with different dilutions of agrobacterial culture containing pICH88266 vector.

Figure 9:
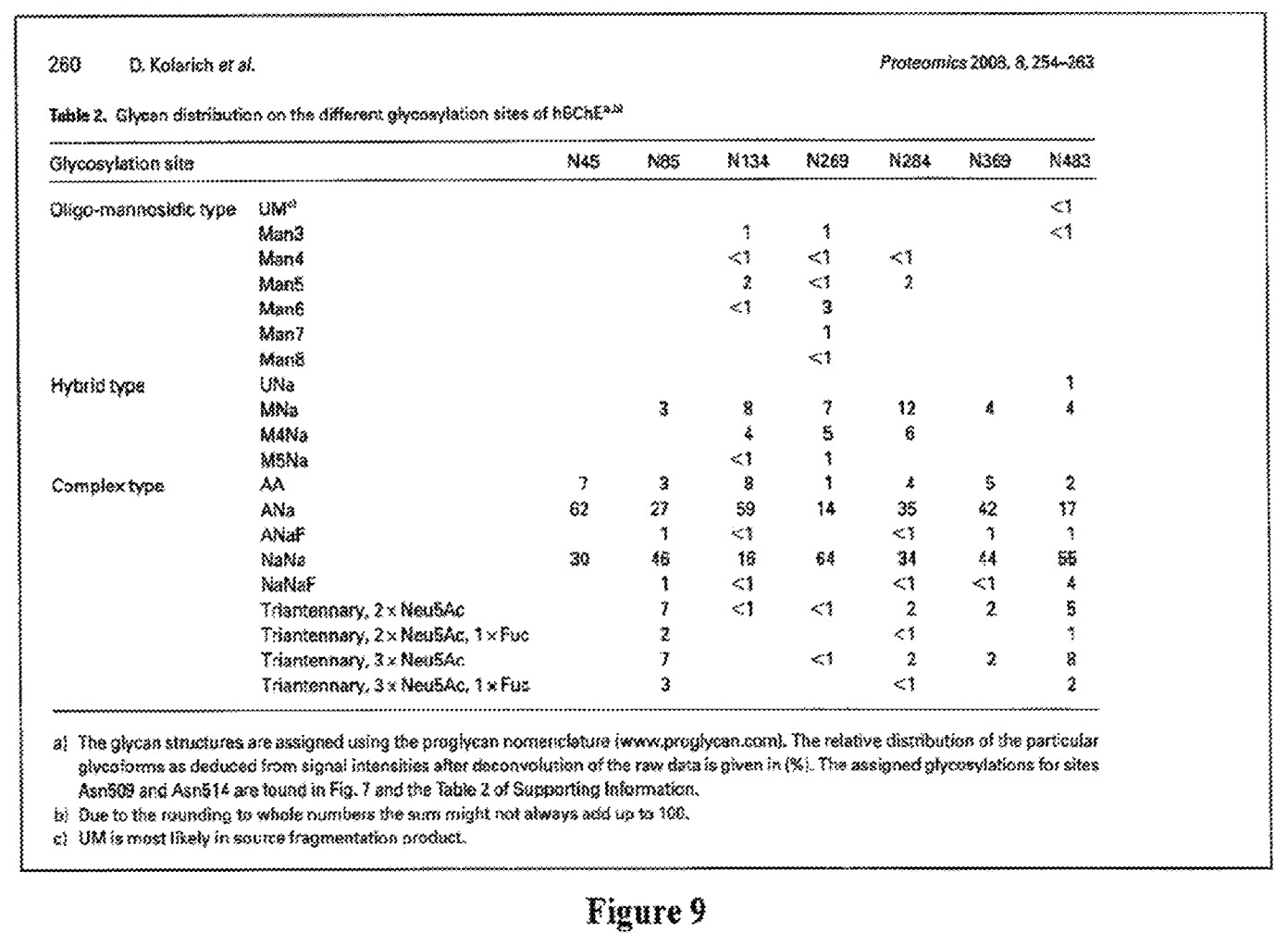

FIG. 9 shows native serum-derived BuChE product data.

Figure 10:
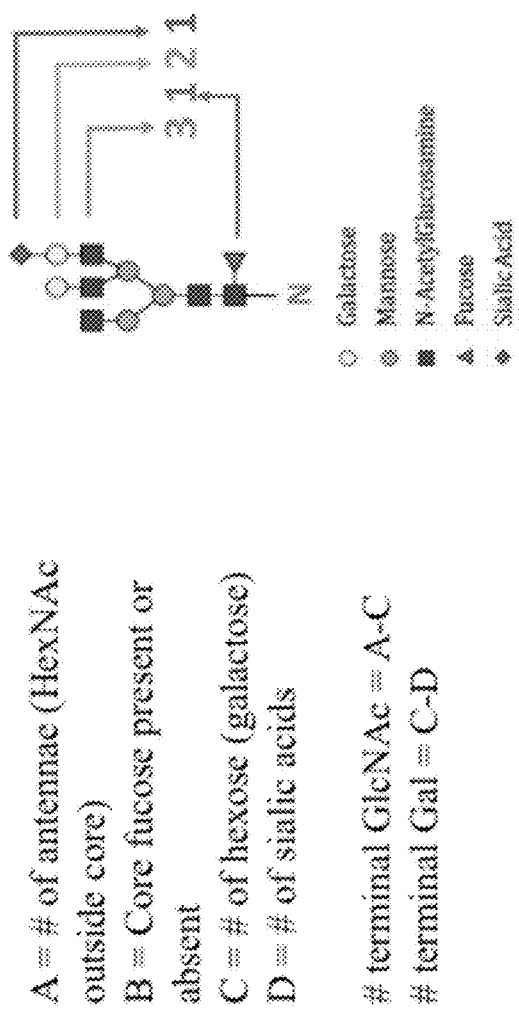

FIG. 10 provides a depiction of nomenclature used for the inventive endogenous sialylated products.

Figure 11:
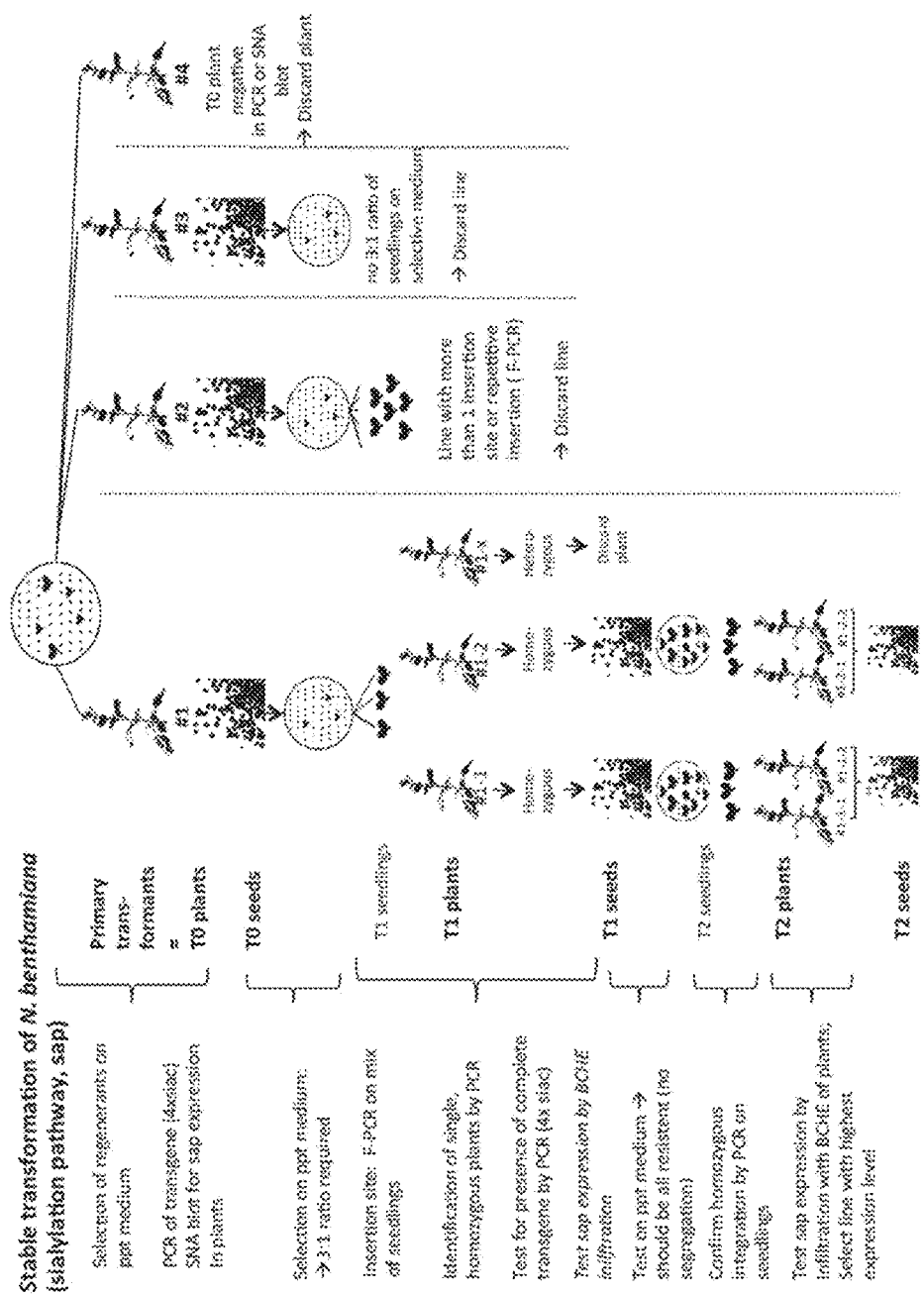

FIG. 11 provides a depiction of the strategy used for transgenic production of exogenous gene sialylation.

Figure 12:
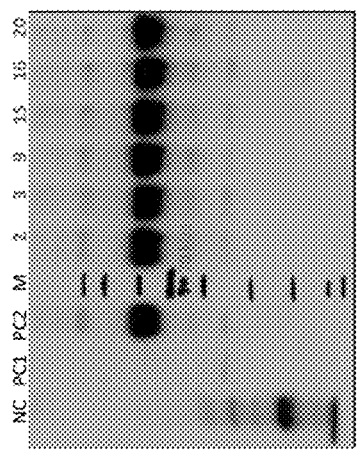

FIG. 12 provides a detailed version of the method of conformation of terminal sialic acid residues of rBuChE produced from SIAL-NbRNAiΔXF-88266#11 plants transfected with transient vectors expressing rBuChE.

Figure 13:
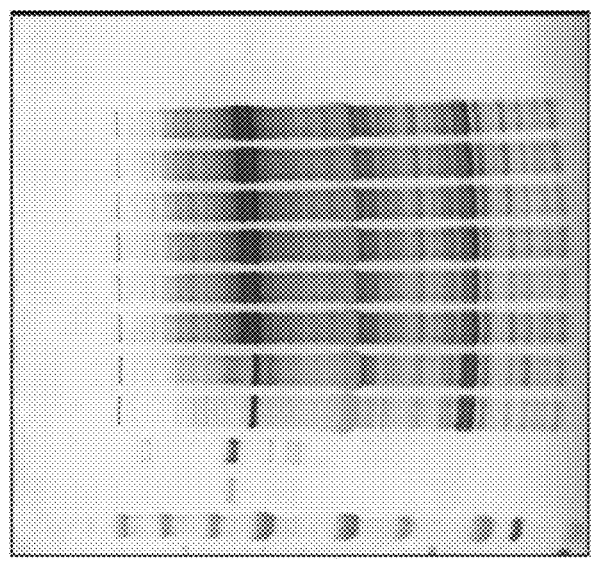

FIG. 13 shows blot results of expression of sialylated rBuChE in T2 plant lines.

Figure 14:
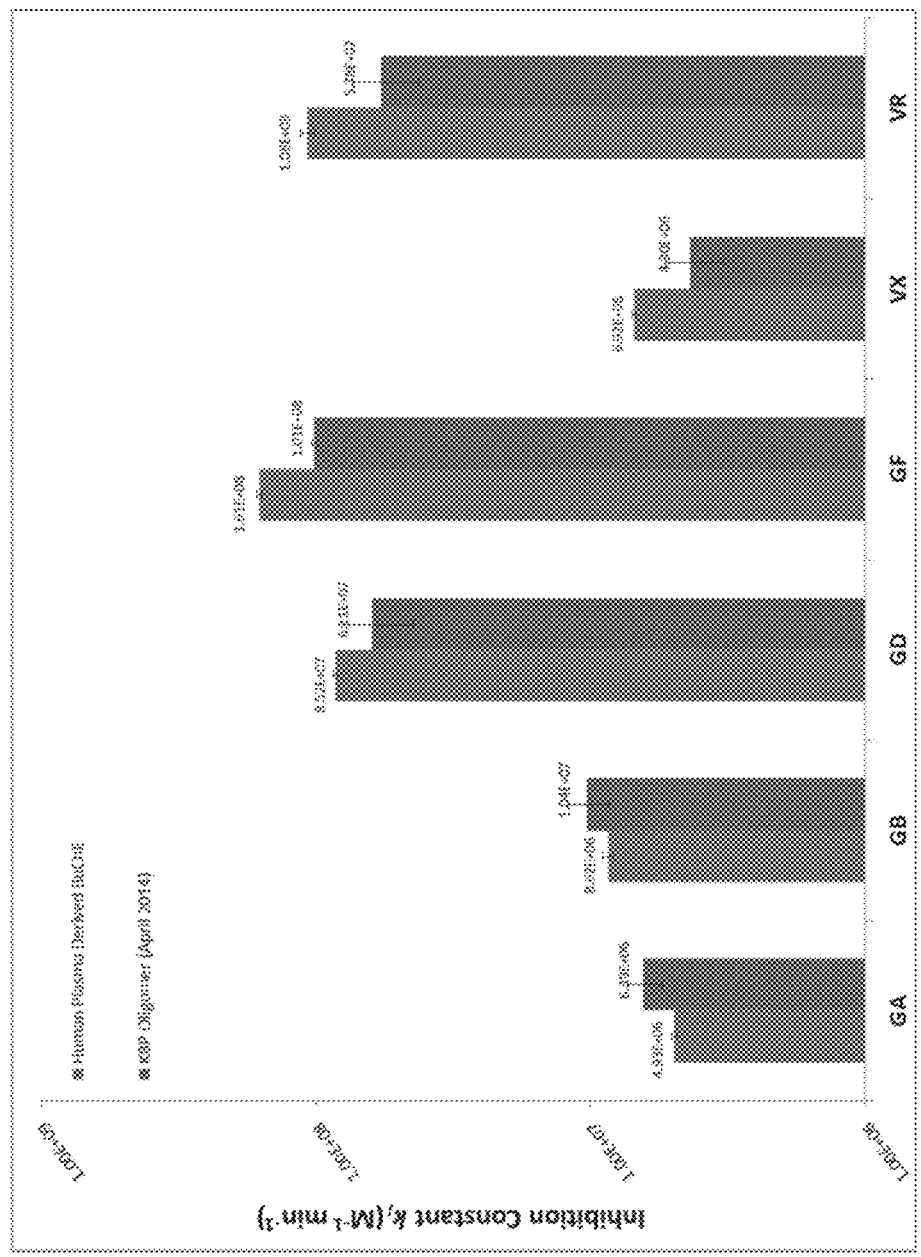

FIG. 14 provides a depiction of the results pertaining to testing the binding of various OP nerve agents, GA, GB, GD, GF, VX and VR, to plant produced, transgenically sialylated rBuChE with plasma derived BuChE.

Figure 15:
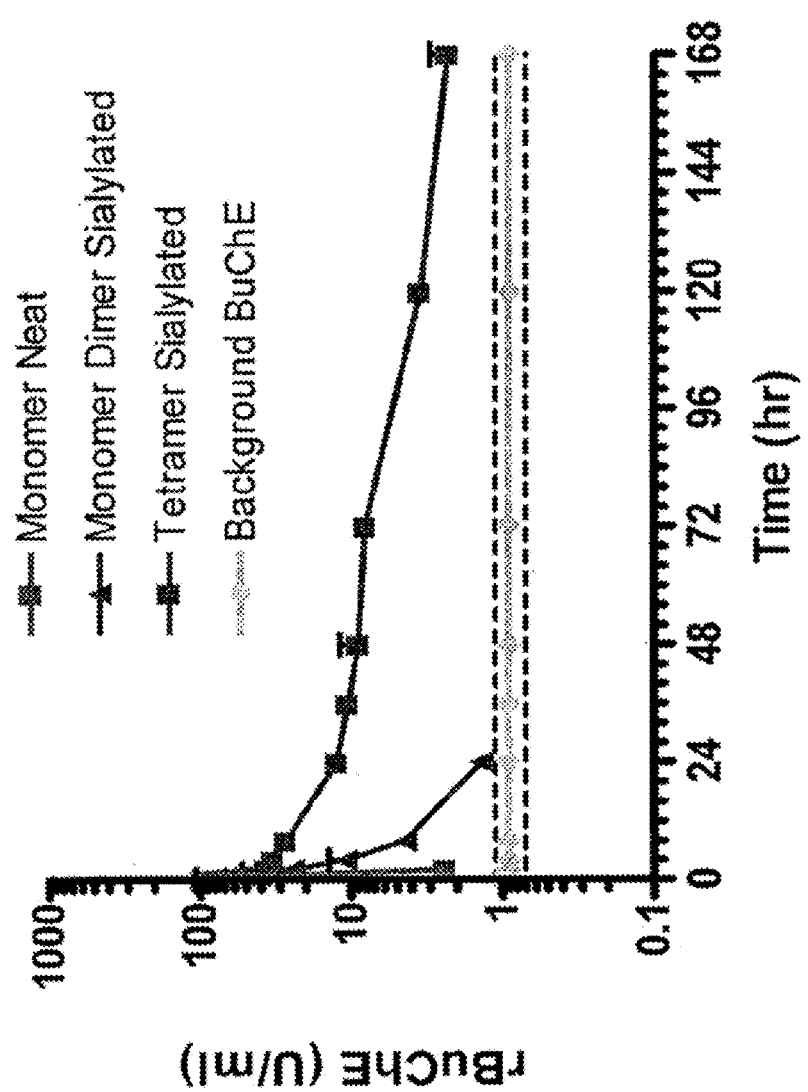

FIG. 15 shows rBuChE activity in plasma from male Hartley guinea pigs administered a single intravenous dose of each variant at 25 mg/kg.

Figure 16:
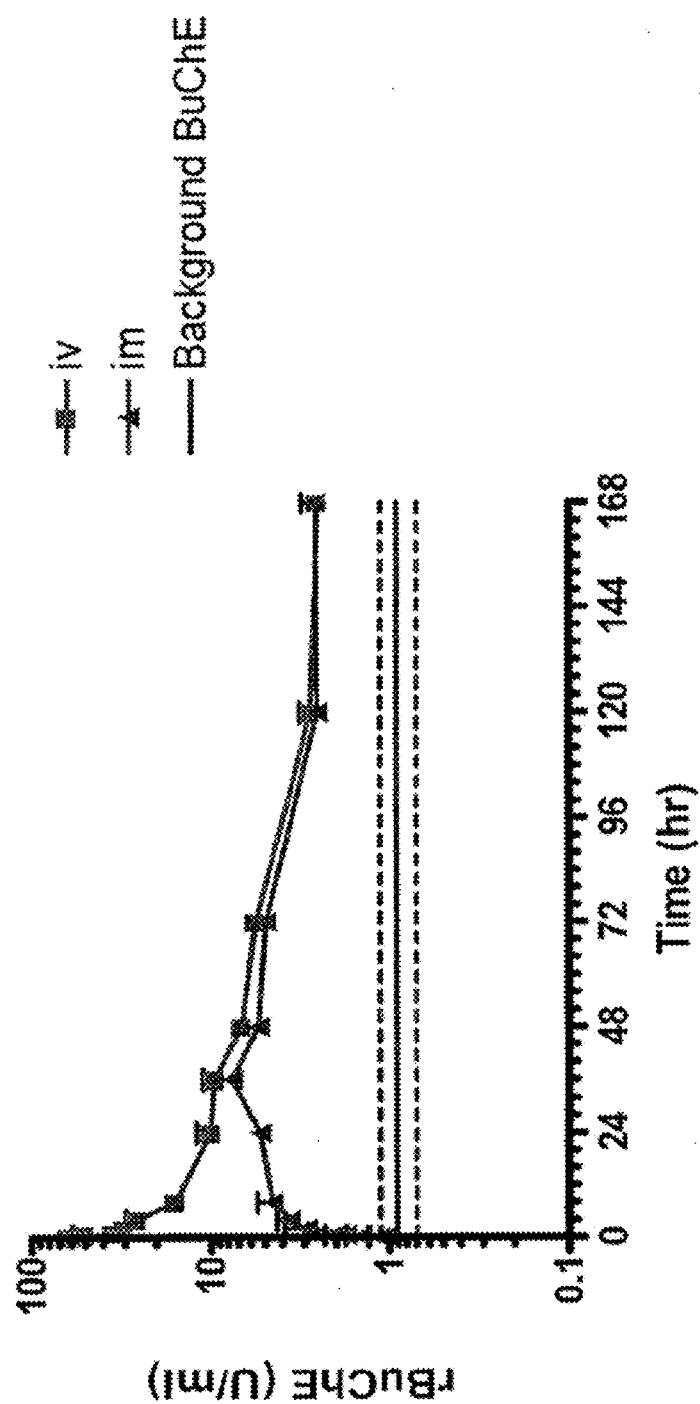

FIG. 16 shows rBuChE activity in plasma of male Hartley guinea pigs administered a single IV or IM dose at 25 mg/kg.

Figure 17:
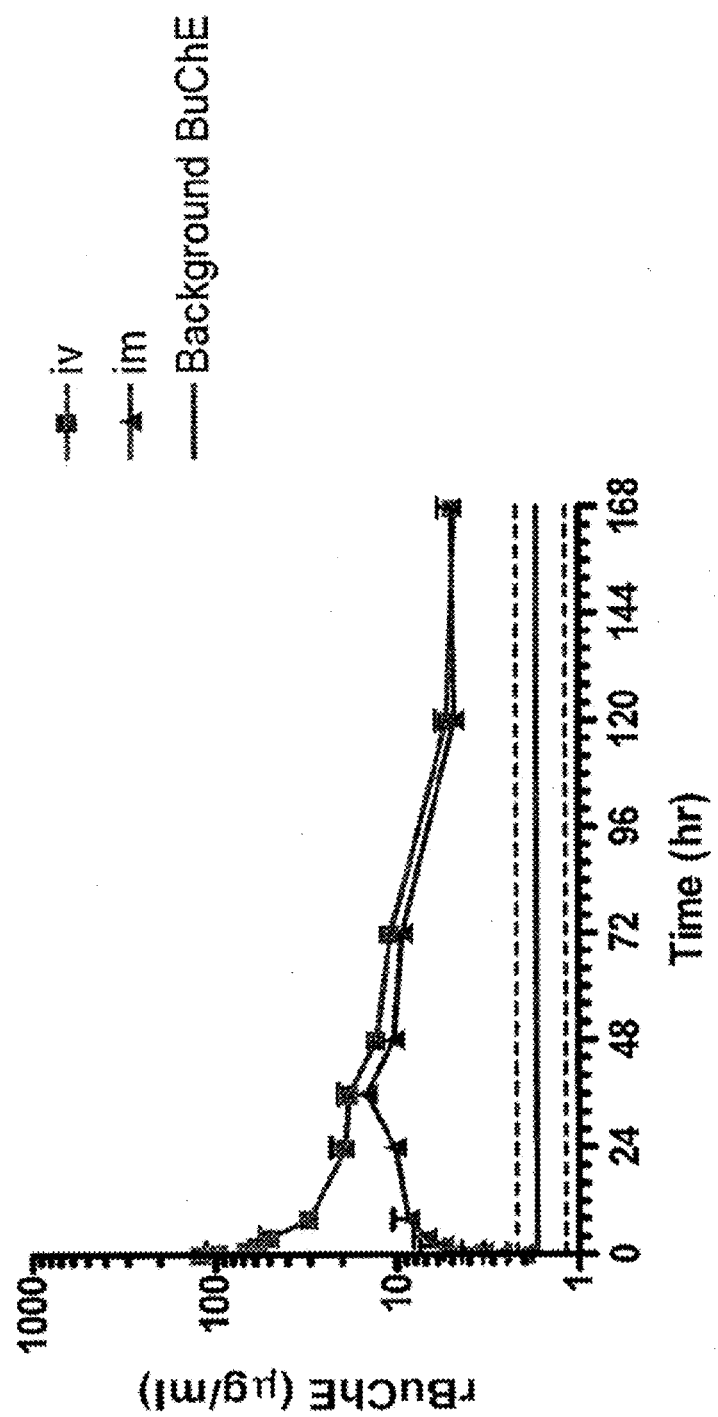

FIG. 17 shows rBuChE activity in plasma of male Hartley guinea pigs administered a single IV or IM dose, 25 mg/kg.

FIG. 18 shows the results of glycan analysis of rBuChE after co-expression with different dilutions of *Agrobacterium* strains harboring the sialylation pathway vector pICH8826.

FIG. 19 shows the glycan content and location of sialylated monomer rBuChE in the identified samples.

FIG. 20 shows an analysis of homozygous plant lines (each SIAL-NbRNAiΔXF) to confirm sialylation ability.

FIG. 21 shows results of seed production of homozygous T1-plants of line SIAL-NbRNAiΔXF-88266#11.

FIG. 22 shows the Sialylation capability of NbRNAiΔXF-88266#11 plant lines as measured by SNA Western blotting and transfection with transient vectors expressing rBuChE.

FIG. 23 shows the observed m/z from FTMS for N-glycans from transgenic sialylated tetramer plant-based rBuChE sample.

DETAILED DESCRIPTION OF THE PREFERRED EMBODIMENTS AND FIGURES

The following descriptions and explanations of the accompanying figures are intended specifically to provide information pertaining to possible embodiments of the present invention. No limitation of the breadth and scope of the overall invention is to be construed by the disclosures provided herein.

As used herein, the following terms are intended to be interpreted as follows:

"transfect" or "transfection" or like word is intended to mean the deliberate introduction of nucleic acids within cells (whether native or non-native) in order to allow for expression of genetic material within such cells;

"vector" or "vectors" or like word is intended to mean a DNA molecule (such as a plasmid, for example) that serves as a vehicle to transfer foreign genetic material into a cell (whether native or non-native), thus allow for gene expression therein;

"expression" or "gene expression" or like word or words is intended to mean the process of transferring information from a gene in order to synthesize a subsequent functional gene product;

"endogenous" is intended to mean originating from within a cell, tissue, or Organism; and "transgenic" or "transgenesis" or like word is intended to mean a process of introducing a gene into a living organism for transfer of a new property that is then passed to the organism's offspring. All transgenic strategies described herein involved the utilization of a vector to allow for gene expression, as well.

Example 1: Production of Monomeric/Dimeric rBuChE in NbRNAiDXF Plants

The inventive production system employs a transient minimal virus-based system launched by infiltration of plants with *Agrobacterium* strains containing a transient plant-virus based production system. The technology and its applications have been described in numerous publications. This transient system (FIG. 1) has proven versatile with demonstrated expression of numerous heterologous proteins, including cytokines, interferon, bacterial and viral antigens, growth hormone, vaccine antigens, single chain antibodies and monoclonal antibodies (mAbs) at levels in excess of 1 gram (g) of total soluble protein per kilogram (kg) of fresh biomass.

Figure 1:
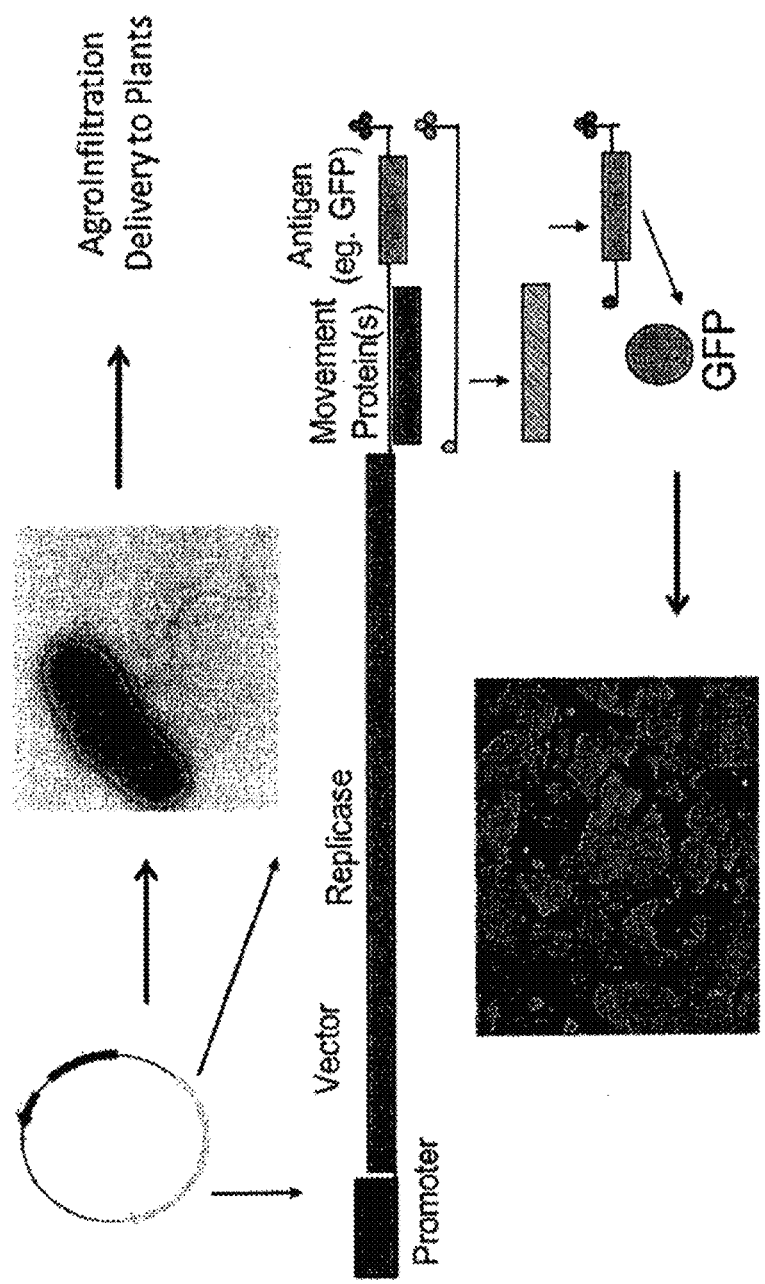

As shown in FIG. 1, the plasmid containing the virus vector (shown in expanded view with gene components and foreign gene insertion—the green fluorescent protein, GFP, described) flanked by the T-DNA borders is illustrated in top left. This plasmid is transfected into *Agrobacterium* strains which are grown and used to infiltrate whole plants, resulting in simultaneous infection of all leaves of the plant with the vector. The *Agrobacterium* delivers the T-DNA to the plant cell nucleus where plant polymerases produce the infectious virus vector transcript which, after transit to the cytoplasm, replicates to high levels independently producing movement proteins for extension of the infection to neighboring cells and production of high levels of recombinant protein (GFP) throughout infiltrated leaves as seen in bottom left panel.

Furthermore, the utilized vectors are built from two different plant virus genomes: TMV-related virus turnip vein clearing tobamovirus (TVCV; FIG. 1) or potato virus X (PVX). The cDNAs of the virus replicons, encoding all the genes required for virus RNA replication, are launched via Agro-infiltration process that initially introduces the virus vectors, carried by the introduced *Agrobacterium* bacterial vector, to many cells throughout the transfected plant. The vector then is "activated" by transcription from the transfer or T-DNA region to produce the virus RNA in vivo and transits it to the cytoplasm for RNA amplification via virus-encoded proteins. These vectors encode requisite proteins for cell to cell movement, including the movement (30K) protein from tobamovirus-based vectors and the triple block products and coat protein for potexvirus-based vectors. These proteins allow movement of the virus vector genome locally within an inoculated leaf resulting in the majority of cells being infected and becoming production sites for the desired protein product in as few as 5-10 days. Aerial parts of the plant are harvested generally by 6-8 days post inoculation (dpi) and extracted for the desired product. For transient rBuChE production, distinct TVCV and PVX vectors in *Agrobacterium* cell lines are used: full length BuChE human gene fused to the barley alpha-amylase signal peptide (pBCHEKBP007; TVCV vector). Although this example detailed expression, accumulation, purification and characterization of wild-type rBuChE, these methods can apply to any BuChE variants, including those which have been optimized for cocaine detoxification (Zheng et al., 2014[17]). Expression of the wild-type rBuChE is performed by transfection of pBCHEKBP007 construct alone results in monomeric rBuChE product.

Figure 2:
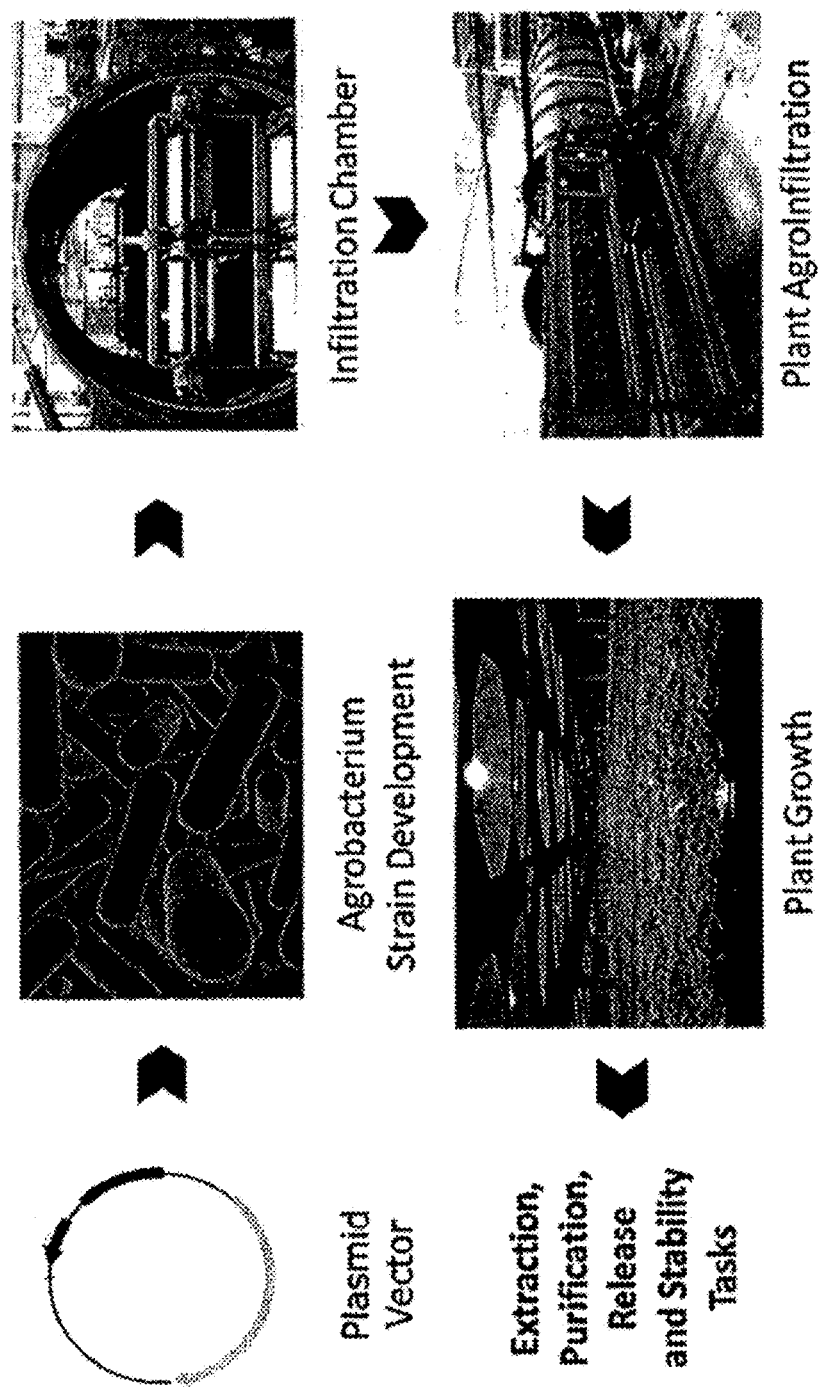

For transient expression of the monomeric rBuChE in plants, *Nicotiana benthamiana* (Nb) plants are infiltrated with *Agrobacterium* strains containing the virus expression vector-encoded plasmids. Nb plants were grown for 24-26 days in an enclosed growth room at 22-24° C. were used for vacuum infiltration. Overnight-grown *Agrobacterium* cultures for rBuChE (Vector ID: pBCHEKBP007) were mixed in the infiltration buffer (10 mM MES, 10 mM MgS0$_4$, pH 5.5). The vector pPBCHKBP007 was diluted 1:1000 (*Agrobacterium* cells: buffer). Production is conducted in wild-type and a transgenic Nb plant line in which RNAi technology was used to knock down both xylose and fucose transferase activities (NbRNAiΔXF). Proteins derived from NbRNAiΔXF plants show highly homogenous mammalian glycoforms such that endogenous and recombinant proteins almost void of any plant-specific fucose or xylose residues. The infiltration solution was transferred into vacuum (infiltration) chambers custom built by Kentucky Bioprocessing (as shown in FIG. 2). The aerial parts of entire plants were submerged upside down into the bacterial/buffer solution and a vacuum of 24" of mercury was applied for 2 min and released. For 80 kg of harvested plant biomass 280 L of infiltration solution was made requiring 280 mL of vector pBCHEKBP007. Post infiltration, plants were returned to the growth room under standard growing conditions. Harvest of the aerial parts of the entire plants occurred at 7 dpi (days post infiltration).

As further shown in FIG. 2, a plasmid vector (top left) is characterized and transformed into *Agrobacterium* strain for MCB and WCB derivation and characterization. WCB is amplified for infiltration and plants are seeded in trays with specially designed lid to permit growth, yet provide a barrier for soil and root components. Following plant growth to appropriate size, trays are loaded on conveyors to enter the vacuum-rated chamber, shown top right with fore and aft doors open and empty. Conveyors rotate 180° and enter the chamber (bottom right), plants are submerged in *Agrobacterium* containing solution and vacuum is applied and released. Plants are removed from chamber, drained of excess solution and rotated to upright position and subsequently transferred to greenhouses for growth and product accumulation, extraction and purification (bottom left).

Furthermore, a scalable extraction, clarification, and non-affinity purification methodology was developed to purify resultant monomeric/dimeric rBuChE. Enzyme extraction was accomplished using mechanical disintegration of infected biomass in the presence of a phosphate buffer. The initial extract was clarified using pH shifting followed by depth filtration employing a plate/frame filter press and diatomaceous earth filter aid. The rBuChE was captured from the clarified extract using Capto Adhere™ multimodal resin (GE Healthcare), with elution accomplished using decreasing pH. The eluent from the capture step was then diluted to low conductivity and applied to Ceramic Hydroxyapatite (CHT) Type I multimodal resin (Bio-Rad Laboratories). The rBuChE was eluted from CHT using an increasing sodium chloride gradient, with host proteins stripped from the column using a high concentration of sodium phosphate. The CHT eluent was incubated with 1% v/v Triton X-114, followed by heating to produce a precipitated detergent phase that contained the majority of endotoxin. The aqueous phase (supernatant) was then removed from the detergent phase and diluted to low conductivity in preparation for final polishing. Residual detergent was removed by binding the rBuChE onto Capto Q™ strong anion exchange resin (GE Healthcare), followed by extensive washing with buffer to fully flush the detergent from the column. Elution of rBuChE from Capto Q was accomplished using an increasing sodium chloride gradient. The Capto Q eluent was then difiltered into phosphate-buffered saline containing arginine, followed by concentration to at least 25 mg/mL using tangential flow ultrafiltration. The bulk drug substance was sterilized using 0.2 μm filtration and stored at 2-8° C.

Figure 3:
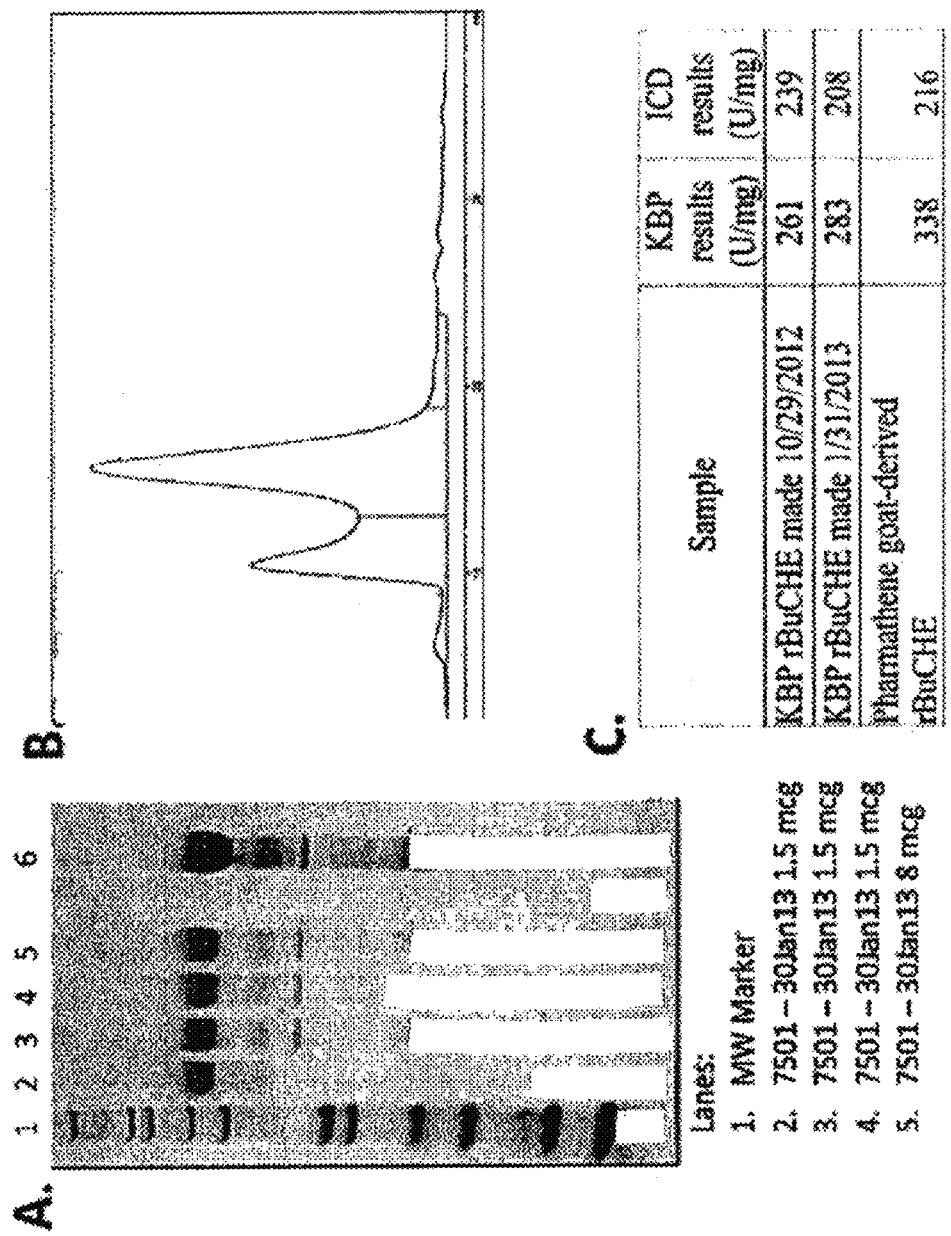

The inventive procedure thus involves the utilization of this plant transient expression technology along with Nb host plants to overexpress rBuChE at levels many-fold higher than published transgenic plant approaches while integrating multigene expression strategies to achieve tetramer formation in rBuChE and host modifications to provide for sialylation of the product in vivo as shown in other examples. This technology system relies on scalable infiltration of Nb plants with *Agrobacterium* strains containing the DNA expression vectors to launch gene expression. This system has been used to produce more than 1 gram quantity lots of monomeric/dimeric rBuChE at >95% purity. This enzyme (produced at ~1.5 gram/lot) shows high enzymatic activity, similar to positive control material purified from transgenic goat sources provided by U.S. Army Medical Research Institute of Chemical Defense, as shown in FIG. 3. In particular, this Figure shows samples from the greater than 1 gram production lot of monomeric rBuChE produced through a plant-derived process as described herein exhibits above 95% purity as shown in A. All non-full length bands are immunoreactive to anti-BuChE antibody indicating product origin. The oligomeric status of the product is shown in B demonstrating greater than 64% monomeric structure. The specific activity of the inventive product compared with the control is shown in C. indicating comparable results with such goat-derived products, as well.

Example 2: Generation of Transient Sialylation Vectors

Multigenic constructs were designed and built to contain genes encoding the proteins to synthesize sialic acid and transfer galactose and sialic acid to terminal N-linked glycan structures in the plant Golgi. FIGS. 4A, 4B, and 4C depict various examples of the inventive transient vector generation procedures. In FIG. 4A, there is shown the plasmid construct pICH88266 consisting of seven expression cassettes, six for the expression of genes required for synthesis and transfer of sialic acid to N-glycans and one selection marker for generation of transgenic plants. Each expression cassette consists of a promoter, a 5' untranslated region (5'UTR), a protein coding sequence (CDS) and a terminator. The various structures are defined as follows: Act2—promoter of *Arabidopsis* Actin 2 gene; Act2ter-transcription termination sequence of *Arabidopsis thaliana* Act 2 gene; CMP-SAS—*Homo sapiens* N-acylneuraminate cytidylyltransferase gene; SPM—promoter of *Zea mays* Spm transposable element MP gene; GCRPter—*Arabidopsis thaliana* GCRP (G-coupled receptor protein) gene transcription termination sequence; BAR—phosphinothricin N-acetyltransferase gene of *Streptomyces hygroscopicus*; Ω—the 5'-untranslated leader sequence (called Omega) of Tobacco Mosaic Virus; NOS—the promoter of the *Agrobacterium tumefaciens* nopalin synthase (nos) gene; NOSter—transcription termination sequence of *Agrobacterium tumefaciens* nopalin synthase (nos) gene; GNE—*Mus musculus* gene encoding for UDP-N-acetylglucosamine-2-epimerase/N-acetylmannosamine kinase; 35 Ster—Cauliflower Mosaic Virus 35S gene transcription termination sequence; SAS—*Homo sapiens* Sialic Acid Synthase gene that catalyzes the synthesis of N-acetylneuramic acid-9-phosphate; 34S—34S promoter of the Figwort Mosaic Virus; Rbcslter—*Arabidopsis thaliana* Rbcs 1 (ribulose-1,5-bisphosphate carboxylase small-subunit) gene transcription termination sequence; CST—*Mus musculus* CMP-Sialic acid Transporter (CST) gene; At RbcslB—promoter of the Rbcsl (ribulose-1,5-bisphosphate carboxylase small-subunit) gene of *Arabidopsis thaliana*; LHB1B2—promoter of the LHB1B1 (light-harvesting chlorophyll protein complex II subunit B 1) gene of *Arabidopsis thaliana*; rST—*Rattus norvegicus* beta-galactoside alpha-2,6-sialyltransferase 1 gene; GAL—*Homo sapiens* β1,4-galactosyltransferase gene; AGSter—agrocinopine synthase (AGS) gene transcription termination sequence from Ti-plasmid of *Agrobacterium tumefaciens*; STLS—promoter of *Solanum tuberosum* STLS (light-inducible tissue-specific) gene; g7 ter—gene 7 transcription termination sequence from *Agrobacterium tumefaciens* T-DNA; rST-.

Assembly of the construct was done using the Golden Gate cloning technology (as shown in Engler et al., 2008[7]) in conjunction with the modular cloning system for multigene constructs (as shown in Weber et al., 2011[15], and within Werner et al., 2011 and 2012[16]). First, all basic elements were cloned in level 0 vectors containing BsaI recognition sites generating 4 bp overlaps specific for each type of module (e.g. AATG and GCTT for CDS modules). The level 0 modules were then assembled into level 1 expression cassettes using the Golden Gate restriction/ligation procedure. Level 1 vectors are framed by BpiI recognition sites specific for one of seven positions defining the order of expression cassettes in the final construct. Two additional positions were covered by two ca. 400 bp random sequences at the beginning and the end which will facilitate the analysis of transgene integration sites. The modular cloning system is designed in such a way that one can assemble six level 1 constructs in one reaction. Since seven genes and two random sequences (i.e. nine level 1 vectors) were required for the final construct, the assembly was done in two steps. The BAR gene expression cassette and the random sequences at both ends were introduced into the destination vector prior to assembly of the other genes.

In the first step, level 1 constructs were assembled via BpiI Golden Gate reaction in two level M vectors (FIG. 4B), respectively, which in turn are framed by compatible Esp3I sites. Thus, in a final reaction, the two level M constructs are assembled in a level P vector to give construct pICH88266 (FIG. 4C, top).

The following basic elements used for pICH88266 are presented in Table 3.

TABLE 3

Expression elements andgenes (CDS-codingregions)
for genes comprised in pICH88266

| Position | Promoter | 5'UTR | CDS | Terminator |
|---|---|---|---|---|
| 1 | Maize Spm | TMV-Ω | BAR (ppt acetyl transferase) | *Arabidopsis* GCRP |
| 2 | Nos | TMV-Ω | GNE (GlcNAc epimerase) | Nos |
| 3 | 34S | TMV-Ω | SAS (sialic acid phosphate synthase) | 35S |
| 4 | Actin2 | TMV-Ω | CMAS (CMP sialic acid synthase) | Actin2 |
| 5 | *Arabidopsis* Rbcs1 | TMV-Ω | CST (CMP sialic acid transporter) | Rbcs1 |
| 6 | *Arabidopsis* LHB1B1 | TMV-Ω | Gal (Galactosyl transferase) | Agrocinopine synthase (Ags) |
| 7 | Potato STLS | TMV-Ω | ST (Sialyl transferase) | g7 |

Example 3: Testing of Transient Sialylation Process for Recombinantly Plant Produced Proteins For transient co-expression of rBuChE (viral expression vector) with sialylation pathway vector pICH88266 normally a 1:10 dilution of the *agrobacterium* overnight culture that harbors the latter vector is used. Viral expression vectors are based on the above-described technology (Gleba, et al., 2005[9]; Gleba et al., 2007[10]); binary vectors developed by Icon Genetics using elements from Tobacco Mosaic Virus (TMV) or Potato Virus X (PVX) (Giritch et al., 2006[8]). Taking into account that pICH88266 is not a viral vector and unable to spread (short distance movement) from infected cells, for large scale infiltration of plants a large volume of *Agrobacterium* culture containing pICH88266 would be required. To investigate the possibility to use smaller amounts of Agrobacteria, an experiment was conducted with higher dilutions of *Agrobacterium* cultures harboring vector pICH88266 which were used for co-expression with the BuChE viral expression vector. Dilutions of 1:10, 1:25, 1:50, 1:100, 1:500 and 1:1000 of overnight cultures (ca. 2 $OD_{600}$) were compared in respect to provide for sialylation of rBuChE.

*Nicotiana benthamiana* wild-type plants were infiltrated with agrobacteria harboring the BuChE viral expression construct (pICH92631) at a 1:1000 dilution and different dilutions of the sialylation pathway construct pICH88266. Prior to purification, crude plant extracts (100 mg plant tissue extracted in 0.3 ml 0.2 M citrate buffer pH6 supplemented with 1 mM EDTA) harvested from 7-days post-infiltration plant tissue were pretested for BuChE activity using an Ellman assay (Ellman, 1961[6]). The results of the pretest are shown in FIG. 5. Within this FIG. 5, the test subjects presented were as follows: Uninfiltrated—plant tissue without any vectors; w/o pICH88266—plant tissue infiltrated only with transient vector expressing BuChE; other columns correspond to plant tissue co-infiltrated with viral vector expressing BuChE and different dilutions of vector pICH88266 (from 10× to 1000× dilutions of o.n. culture).

Figure 6:
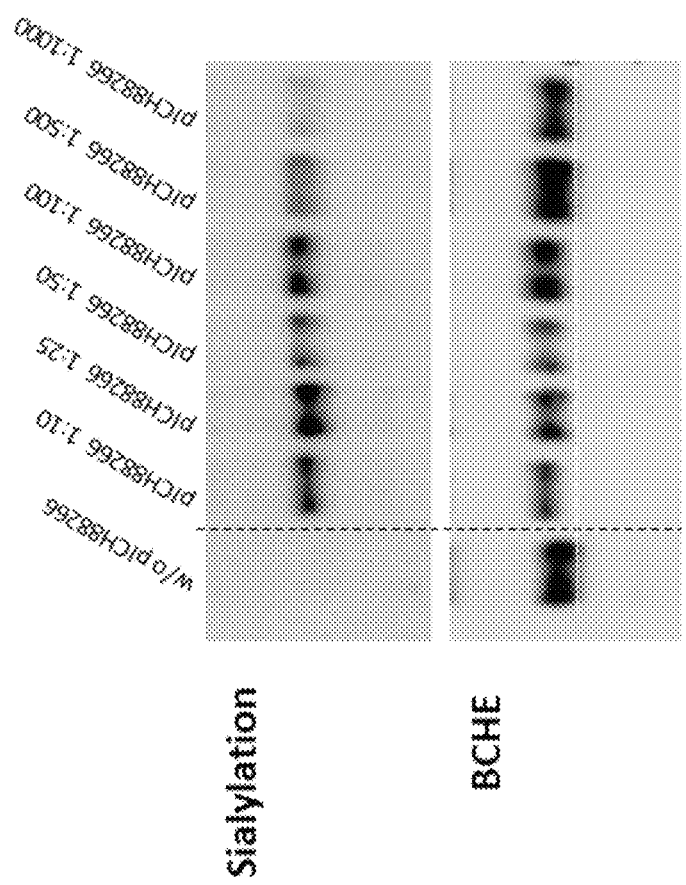
FIG. 6 shows a Western blot analysis rBuChE sialylation level for different dilutions of pICH88266 vector providing for sialylation pathway within the inventive production method.

After this pretest, the His-tagged BCHE was purified from the different samples using Ni-NTA chromatography. Comparable amounts of purified BCHE (~2 µg each) were separated on polyacrylamide gels supplemented with SDS, blotted on PVDF membranes and probed with biotinylated SNA lectin (*Sambucus nigra* lectin that binds preferentially to sialic acid attached to terminal galactose in α-2,6 and to a lesser degree, α-2,3 linkage of sialic acid to glycans; Vector laboratories, Peterborough, UK) and streptavidin-HRP conjugate (Life Technologies, Darmstadt, Germany) for detection of sialic acid. To confirm the detection of sialylated rBuChE, the membranes were stripped and reprobed with a goat anti-BCHE polyclonal antibody (Santa Cruz Biotechnology, Heidelberg, Germany) and anti-goat IgG-peroxidase conjugate (Sigma-Aldrich, St. Louis, USA). Sialylation of rBuChE was detected for all tested dilutions, but stronger for dilutions 1:10 up to 1:100. Additionally, a shift in protein size corresponding to rBuChE sialylation was visible for dilutions 1:10 up to 1:100. The results of Western blot analyses are shown in FIG. 6. Within this Figure, the upper panel shows a Western blot of purified rBuChE isolated from leaves co-infiltrated with different dilutions of *agrobacterium* carrying pICH88266. The blot was probed with biotinylated SNA lectin (*Sambucus nigra* lectin; Vector laboratories, Peterborough, UK) and streptavidin-HRP conjugate (Life Technologies, Darmstadt, Germany) for detection of sialic acid. The lower panel shows the same blot reprobed with a goat anti-BuChE polyclonal antibody (Santa Cruz Biotechnology, Heidelberg, Germany) and anti-goat IgG-peroxidase conjugate (Sigma-Aldrich, St. Louis, USA).

These results show that higher dilutions up to 1:100 of the agrobacteria containing pICH88266 could be used in principle; however, results were not quantitative. Therefore, MALDI analysis of samples with pICH88266 dilutions of 1:10, 1:25, 1:50 and 1:100 was conducted. Analysis of the free glycans showed for all analyzed dilutions a similar content of sialylation (1:10 dilution: 46%; 1:25 dilution: 49%; 1:50 dilution: 57%; 1:100 dilution: 42%, details are provided more effectively in FIG. 18). In conclusion, a 1:50 or even a 1:100 dilution of agrobacteria harboring pICH88266 could be used for large scale production of BCHE.

Figure 7:
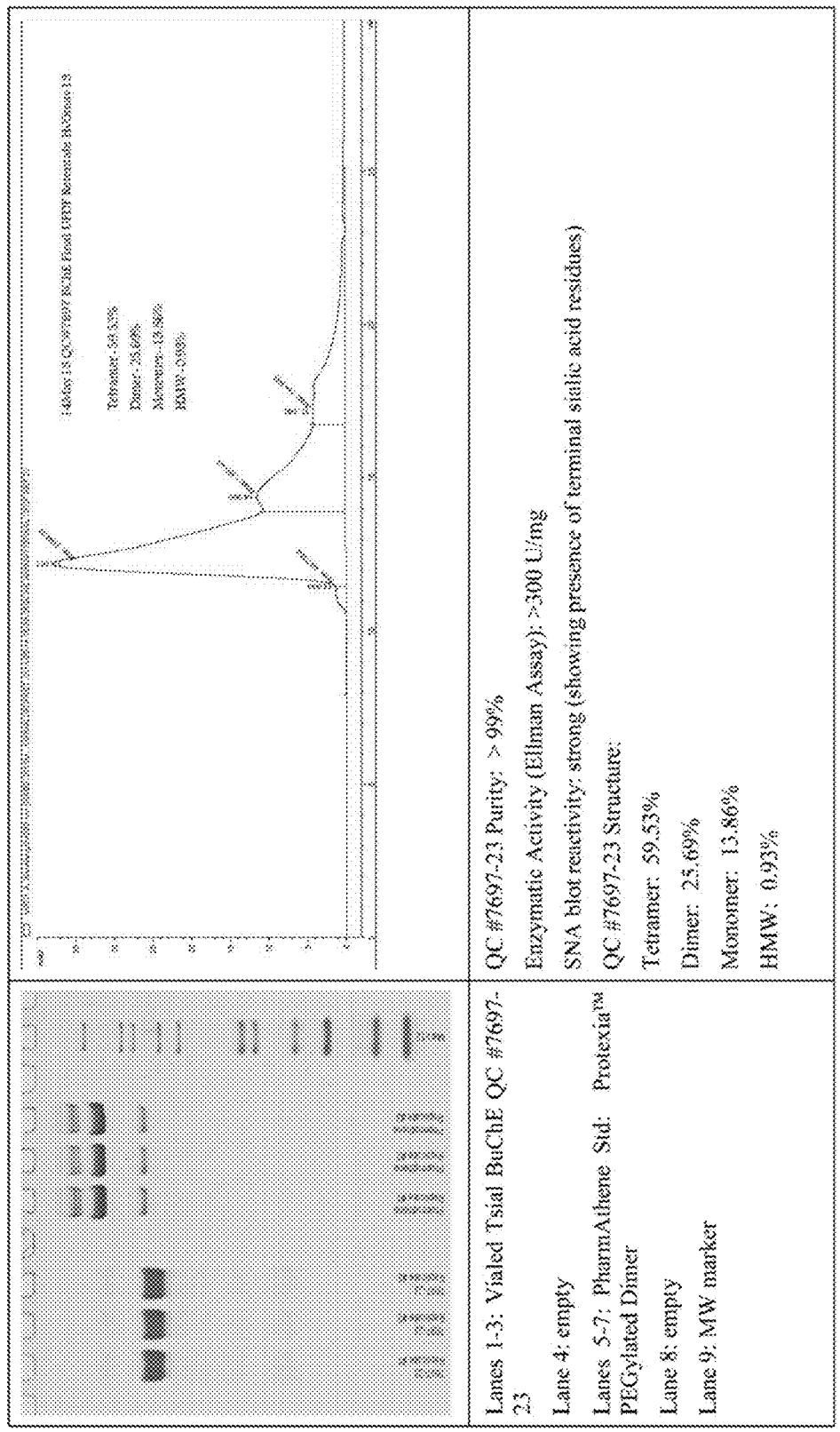
FIG. 7 shows measurements of properties of inventive sialylated tetramer products produced by a possible embodiment of the method described herein.

Example 4: Production of Transiently Sialylated Tetramer form of rBuChE in ΔXTFT *N. benthamiana* (80 kg Plant Biomass) Using Transient Sialyalation methods Sialylation of rBuChE can be achieved using either (a) transient or (b) transgenic strategies. Transient strategies (a) involve the co-transfection of pBCHEKBP007 alone, or with polyproline adhesion domain (PRAD) peptide expressing vectors (as described above for monomeric or tetrameric product, respectively), along with the pICH88266 plant expression vector in appropriate *Agrobacterium* stains. PRAD peptides were identified in association with human and equine BuChE (Duysen et al., 2002[5]; Li et al., 2008[12]; Ilyushina et al., 2013[11]). Experiments in mammalian cells suggest that co-expression of PRAD peptides can produce increased levels of tetramerized rBuChE. However, to date, no one has produced an efficiently tetramerized, sialylated rBuChE in mammalian cells (see references above). The method described below demonstrate that PRAD co-expression with rBuChE results in high proportion in excess of 60% rBuChE tetramer formation that can be sialylated by transient and transgenic methodologies efficiency (with about 70% of linkages sialylated).

The pICH88266 plasmid contains expression constructs for the seven genes to allow sialic acid to be synthesized, functionalized and transferred to nascent glycan strains in the plant Golgi apparatus along with the BAR selectable marker gene.

For producing tetramer rBuChE, co-transfection with a transient vector expressing a PRAD or tetramerizing peptide were tested. The following PRAD Sequences (amino acid) were used to produce genetic constructs for expression in planta:

```
1.
                                          "(SEQ ID NO: 1)"
mankhlslslflvllglsaslasgAPSPPLPPPPPPPPPPPPPPPP
PPPLP 2.
                                          "(SEQ ID NO: 2)"
mankhlslslflvllglsaslasgACCLLMPPPPPLFPPPFF 3.
                                          "(SEQ ID NO: 3)"
mankhlslslflvllglsaslasgACCLLMPPPPPLFPPPFFDYKDD
DDK 4.
                                          "(SEQ ID NO: 4)"
mankhlslslflvlglsaslasgAQPTFINSVLPISAALPGLDQKKR
GNHKACCLLMPPPPPLFPPPFF
```

All four genes were optimized for Nb codon bias and synthesized. Of these, PRAD peptide 1 (derived from Lamellipodin) and PRAD peptide 4 (derived from collagen-like ColQ) were successfully cloned into PVX transient vectors. Unfortunately, PRAD peptide constructs encoding proteins 2 and 3 were not successfully cloned. Both constructs produced tetramer-like protein, and PRAD peptide 4 was chosen for continued testing due to time constraints.

For transient expression of the Tetramer-sialylated rBuChE in plants, the transfection procedure described above was used with minor modifications. Plants grown for 24-26 days in an enclosed growth room at 22-24° C. were used for vacuum infiltration. Overnight-grown *Agrobacterium* cultures for rBuChE (Vector ID: pBCHEKBP007), the tetramerizing peptide from ColQ (Vector ID: Tetra 4; [both ColQ and Lamellipodin vectors where shown to work similarly in other studies]) and the sialylation pathway (Vector ID: pICH88266) were mixed in the infiltration buffer (10 mM MES, 10 mM $MgSO_4$, pH 5.5). The vector pPBCHKBP007 was diluted 1:1000 (*Agrobacterium* cells:buffer), Tetra 4 was diluted 1:200 (*Agrobacterium* cells:buffer) and pICH88266 was diluted 1:10 (*Agrobacterium* cells:buffer). The infiltration solution was transferred into custom built (Kentucky Bioprocessing, Owensboro, Ky.) vacuum chambers. The aerial parts of entire plants were submerged upside down into the bacterial/buffer solution and a vacuum of 24" of mercury was applied for 2 min and released. For 80 kg of harvested plant biomass 280 L of infiltration solution was made requiring 280 mL of vector pBCHEKBP007, 1.4 L of vector Tetra 4 and 28 L of vector pICH88266. Post infiltration, plants were returned to the growth room under standard growing conditions. Harvest of the aerial parts of the entire plants occurred at 7 dpi (days post infiltration).

A scalable extraction, clarification, and non-affinity purification methodology was developed to purify Tetramer rBuChE. Enzyme extraction was accomplished using mechanical disintegration of infected biomass in the presence of a phosphate buffer. The initial extract was clarified using pH shifting followed by depth filtration employing a plate/frame filter press and diatomaceous earth filter aid. The rBuChE was captured from the clarified extract using Capto Adhere™ multimodal resin (GE Healthcare), with elution accomplished using decreasing pH. The eluent from the capture step was then diluted to low conductivity and applied to Ceramic Hydroxyapaptite (CHT) Type I multimodal resin (Bio-Rad Laboratories). The rBuChE was eluted from CHT using an increasing sodium chloride gradient, with host proteins stripped from the column using a high concentration of sodium phosphate. The CHT eluent was incubated with 1% v/v Triton X-114, followed by heating to produce a precipitated detergent phase that contained the majority of endotoxin. The aqueous phase (supernatant) was then removed from the detergent phase and diluted to low conductivity in preparation for final polishing. Residual detergent was removed by binding the rBuChE onto Capto Q™ strong anion exchange resin (GE Healthcare), followed by extensive washing with buffer to fully flush the detergent from the column. Elution of rBuChE from Capto Q was accomplished using an increasing sodium chloride gradient. The Capto Q eluent was then diafiltered into phosphate-buffered saline containing arginine, followed by concentration to at least 25 mg/mL using tangential flow ultrafiltration. The bulk drug substance was sterilized using 0.2 μm filtration and stored at 2-8° C. Final product properties are shown in FIG. 7.

In this situation, however, it was determined that the plant-based methodologies described herein involving transient rBuChE expression with PRAD peptides with the transient sialylation system or in transgenic plants (such as within Example 5 below, as one non-limiting example) produce highly sialylated products that accumulate throughout transfected plant cells and can be readily, not just selectively, isolated. This inventive technological breakthrough is thus not only highly unexpected in terms of viability, scalability, and reliability, but is also more efficient for producing material sufficient for detailed animal studies for OPs treatment analyses, and further is also highly cost effective (reducing overall production costs by potentially 10-100 fold compared with serum-derived enzyme BuChE products).

Example 5: Production of Transiently Sialylated Monomer form of rBuChE in ΔXTFT *N. benthamiana* (80 kg Plant Biomass) Using Transient Sialyalation Methods For transient expression of the monomer-sialylated rBuChE in plants, the transfection procedure as described above was used with minor modifications. Plants grown for 24-26 days in an enclosed growth room at 22-24° C. were used for vacuum infiltration. Overnight-grown *Agrobacterium* cultures for rBuChE (Vector ID: pBCHEKBP007) and the sialylation pathway (Vector ID: pICH88266) were mixed in the infiltration buffer (10 mM MES, 10 mM MgS0$_4$, pH 5.5). The vector pPBCHKBP007 was diluted 1:1000 (*Agrobacterium* cells:buffer and pICH88266 was diluted 1:10 (*Agrobacterium* cells:buffer). The infiltration solution was transferred into custom built (Kentucky Bioprocessing, Owensboro, Ky.) vacuum chambers. The aerial parts of entire plants were submerged upside down into the bacterial/buffer solution and a vacuum of 24" of mercury was applied for 2 min and released. For 80 kg of harvested plant biomass 280 L of infiltration solution was made requiring 280 mL of vector pBCHEKBP007 and 28 L of vector pICH88266. Post infiltration, plants were returned to the growth room under standard growing conditions. Harvest of the aerial parts of the entire plants occurred at 7 dpi (days post infiltration).

A scalable extraction, clarification, and non-affinity purification methodology was developed to purify Monomer-sialylated rBuChE. Enzyme extraction was accomplished using mechanical disintegration of infected biomass in the presence of a phosphate buffer. The initial extract was clarified using pH shifting followed by depth filtration employing a plate/frame filter press and diatomaceous earth filter aid. The rBuChE was captured from the clarified extract using Capto Adhere™ multimodal resin (GE Healthcare), with elution accomplished using decreasing pH. The eluent from the capture step was then diluted to low conductivity and applied to Ceramic Hydroxyapatite (CHT) Type I multimodal resin (Bio-Rad Laboratories). The rBuChE was eluted from CHT using an increasing sodium chloride gradient, with host proteins stripped from the column using a high concentration of sodium phosphate. The CHT eluent was incubated with 1% v/v Triton X-114, followed by heating to produce a precipitated detergent phase that contained the majority of endotoxin. The aqueous phase (supernatant) was then removed from the detergent phase and diluted to low conductivity in preparation for final polishing. Residual detergent was removed by binding the rBuChE onto Capto Q™ strong anion exchange resin (GE Healthcare), followed by extensive washing with buffer to fully flush the detergent from the column. Elution of rBuChE from Capto Q was accomplished using an increasing sodium chloride gradient. The Capto Q eluent was then diafiltered into phosphate-buffered saline containing arginine, followed by concentration to at least 25 mg/mL using tangential flow ultrafiltration. The bulk drug substance was sterilized using 0.2 μm filtration and stored at 2-8° C.

Figure 8:
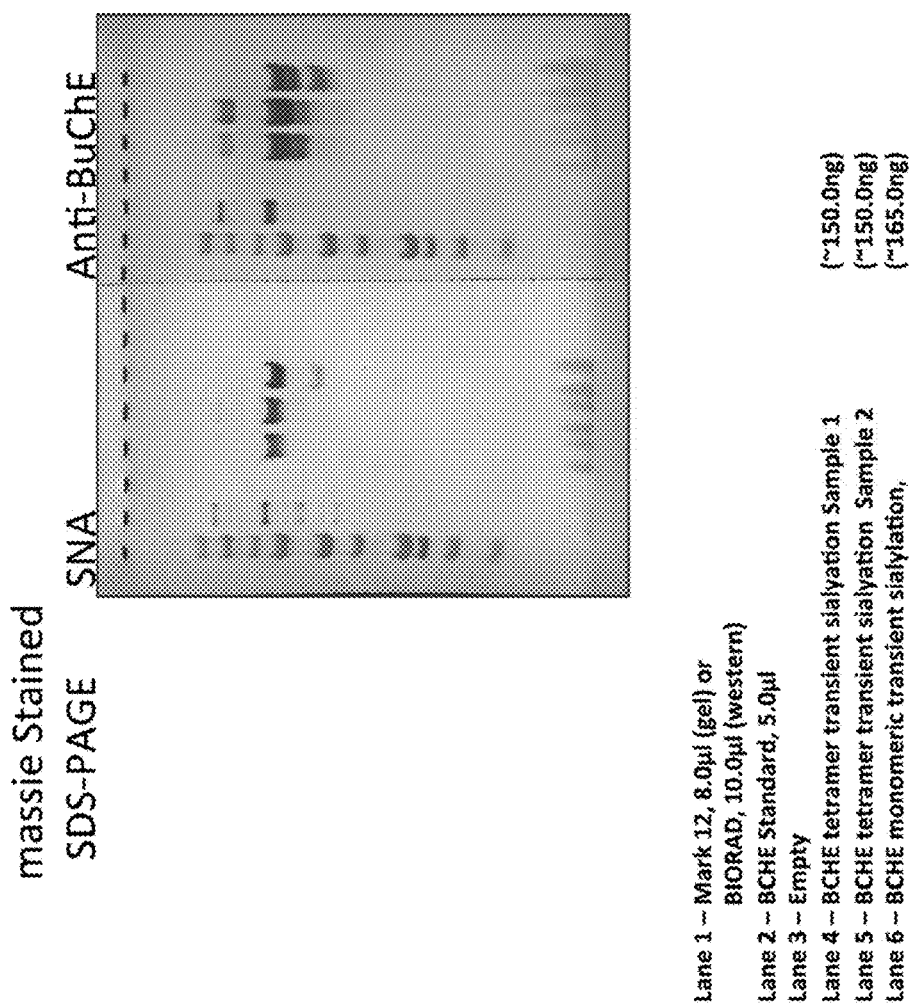
FIG. 8 depicts a demonstration of sialylation of monomeric and tetrameric rBuChE using transient co-expression methods.

The SNA reactivity to final purified product is similar for both monomeric and tetrameric protein products. These data are encouraging for the potential efficacy of the transiently sialylated product as well as the potential for increased sialylation from the new transgenic plant strains. These data suggest that significant in vivo sialylation is possible using the transgenic plant production strategy (such as in FIG. 8). FIG. 8 provides a demonstration of sialylation of monomeric and tetrameric rBuChE using transient co-transfection methods. In this manner, Nb plants were co-transfected with pBCHEKBP007 & pICH88266, encoding rBuChE and the sialylation pathway for a monomeric product and pBCHEKBP007, pICH88266 and the PVX transient vector expressing the ColQ PRAD peptide for the production of a tetrameric product. Sialylation was determined by sandwich Western blotting using *Sambucus nigra* lectin that binds sialic acid terminal glycans and rBuChE was also measured by anti-BuChE anti-sera. The purity of each sialylated monomer and tetramer was greater than 95% product in terms of related proteins. The specific activities of the sialylated monomer and tetramer were measured to be 338 and 392 U/mg, respectively. SEC chromatography also showed that the rBuChE product was more than 60% tetramer in form. Methods for determining purity, oligomeric state, and activity for recent production lots were similar to that shown in FIG. 7 as well as expected results for monomeric and or dimeric product(s).

The native serum-derived BuChE is shown in FIG. 9. These data shows high levels of endogenous sialylated residues (see FIG. 10 for the nomenclature used for description purposes with this data). Analysis was undertaken of the glycan composition of the monomeric rBuChE produced using transient sialylation system using tryptic peptide and glycan analysis using LC MS/MS methods. Use of the transient sialylation process (a) using the pBCHEKBP007 vector shows remarkably high levels of sialylation with an excess of 45% of all glycans showing single or multiple sialic acid residues on terminal glycan structures (as shown in FIG. 18). This is approximately 60% of the total sialylation observed in human plasma BuChE. The similar SNA intensity between monomer and tetramer rBuChE suggests a similar amount of sialylation in monomer and tetramer product.

Example 6: Glycan Analysis of Transiently Sialylated Monomer/Dimer rBuChE

Glycan analysis of dialyated monomer protein was carried out as described: the LC/MS setup for separation of the enzyme digest consisted of a capillary HPLC using a 1 mm×150 cm C18 reverse phase column with formic acid (FA) mobile phase and acetonitrile gradient elution. The detection of peptide and glycopeptide ions is by mass detection in a quadrupole time of flight (QTOF) mass spectrometer. The tryptic maps of the resulting glycopeptide ion spectra are used to identify specific glycan structures by comparison of the observed ion mass to the predicted mass. The expected peptides resulting from trypsin digest were analyzed for N-link glycosylation. The Base Peak tryptic map of Lot 13B003, Lot 13B005, monomeric sialylated rBuChE, and CHT Elution were determined. The tryptic maps have notable differences. Monomeric, sialylated rBuChE, and CHT Elution were analyzed separately from Lot 13B003 and 13B005. For the 13B003 and 13B005 lots were analyzed using an optimized gradient to capture the early eluting glycopeptides. The samples were comparable when they were analyzed using the same gradient.

BuChE has nine potential N-Link sites, the present study focused on the identity and quantitation of glycan species on five of the N-Link sites presented in FIG. 19 and Table 6. Asn17, Asn57, Asn256, Asn341 and Asn455 were the subject of analysis. The tryptic peptides derived are shown in FIG. 18 (all structures identified on all sites) and FIG. 21 (dominant glycan structure is shown and occupancy percentage reported for each site). The average levels of sialylation, non-sialylation and aglycosylation associated with glyocopeptides derived from the five analyzed Asns are shown in FIG. 19. The occupancy of the major glycan structures for each of the five sites are shown in FIG. 19 and Table 6. For comparison, glycan structures associated with serum-derived BuChE are shown in FIG. 9. For FIG. 19 and Table 6, nomenclature for plant-derived glycan structures is described in FIG. 10. Difficulty was experienced in analyzing peptides and structures associated with Asn106, Asn481 and Asn486.

The native serum-derived BuChE is shown in FIG. 9. These data shows high levels of endogenous sialylated residues. Analysis was then undertaken of the glycan composition of the monomeric rBuChE produced using transient sialylation system using tryptic peptide and glycan analysis using LC MS/MS methods. Use of the transient sialylation process (a) using the p8CHEK8P007 vector shows remarkably high levels of sialylation (structures exhibiting more than 70% of all glycans showing single or multiple sialic acid residues on terminal glycan structures)(FIG. 19 and Table 6). This is approximately 70% of the total sialylation observed in human plasma BuChE. The similar SNA intensity between monomer and tetramer rBuChE suggests a similar amount of sialylation in monomer and tetramer product.

Glycan analysis of dialyated monomer protein was carried out as described: the LC/MS setup for separation of the enzyme digest consisted of a capillary HPLC using a 1 mm×150 cm C18 reverse phase column with formic acid (FA) mobile phase and acetonitrile gradient elution. Detection of peptide and glycopeptide ions is by mass detection in a quadrupole time of flight (QTOF) mass spectrometer. The tryptic maps of the resulting glycopeptide ion spectra are used to identify specific glycan structures by comparison of the observed ion mass to the predicted mass. The expected peptides resulting from trypsin digest were analyzed for N-link glycosylation. The Base Peak tryptic map of Lot 13B003, Lot 13B005, monomeric sialylated rBuChE, and CHT Elution were determined. The tryptic maps have notable differences. Monomeric, sialylated rBuChE and CHT Elution were analyzed separately from Lot 13B003 and 13B005. For the 13B003 and 13B005 lots were analyzed using an optimized gradient to capture the early eluting glycopeptides. The samples were comparable when they were analyzed using the same gradient.

BuChE has nine potential N-Link sites, the present study focused on the identity and quantitation of glycan species on five of the N-Link sites presented in FIG. 19. Asn17, Asn57, Asn256, Asn341 and Asn455 were the subject of analysis. The tryptic peptides derived are shown in FIG. 19 (all structures identified on all sites) and Table (dominant glycan structure is shown and occupancy percentage reported for each site). The average levels of sialylation, non-sialylation and aglycosylation associated with glyocopeptides derived from the five analyzed Asns are shown in FIG. 19. The occupancy of the major glycan structures for each of the five sites are shown in Table 6. For comparison, glycan structures associated with serum-derived BuChE is shown in FIG. 12. For FIG. 19 and Table 6, nomenclature for plant-derived glycan structures is described in FIG. 13. Difficulty was experienced in analyzing peptides and structures associated with Asn106, Asn481 and Asn486.

TABLE 6

Monomeric rBuChE Transiently Expressed Glycan Forms Tryptic Glycopeptides Msial Formulated Sum of all N-Link Sites

| Glycan | Total Vol | Area % |
|---|---|---|
| 0000 | 9,890,025 | 8.3 |
| 1000 | 9,436,467 | 7.9 |
| 1100 | 552,364 | 0.5 |
| 2002 | 2,483,922 | 2.1 |
| 2010 | 484,716 | 0.4 |
| 2011 | 1,659,161 | 1.4 |
| 2020 | 112,697 | 0.1 |
| 2021 | 2,645,798 | 2.2 |
| 2022 | 77,606,591 | 64.9 |
| 21 10 | 191,087 | 0.2 |
| 2120 | 179,291 | 0.1 |
| 2121 | 1,198,000 | 1.0 |
| 2122 | 1,050,067 | 0.9 |
| Agly | 12,110,846 | 10.1 |
|  | 119,601,032 | 100.0 |
| Sialylated |  | 70.4% |
| Non-Sialylated |  | 19.5% |
| Aglycosylated |  | 10.1% |

The native serum-derived BuChE is shown in FIG. 12. These data shows high levels of endogenous sialylated residues. We analyzed the glycan composition of the monomeric rBuChE produced using transient sialylation system using tryptic peptide and glycan analysis using LC MS/MS methods. Use of the transient sialylation process (a) using the pBCHEKBP007 vector shows remarkably high levels of sialylation—greater than 70% of all glycans showing single or multiple sialic acid residues on terminal glycan structures (FIG. 19 and Table 6). This is approximately 70% of the total sialylation observed in human plasma BuChE. The similar SNA intensity between monomer and tetramer rBuChE suggests a similar amount of sialylation in monomer and tetramer product.

Further analysis was undertaken of both mono- and oligo-saccharide constituents on transiently sialylated tetramer products generated through this general method. The glycan structures were basically analyzed for content and whether the transient production scheme accorded effective and high occupancy measurements for optimal OPs effectiveness.

The collected samples were dialyzed against running deionized water for about 24 hours through a 4-kDa membrane. After dialysis, the samples were then lyophilized in preparation for monosaccharide composition analysis. Subsequently, an aliquot of each sample was allocated for neutral and amino sugars analysis (~200 µg), and for sialic acids analysis (~200 µg). The aliquots for neutral and amino sugars were hydrolyzed with 2.0 N trifluoroacetic acid (TFA), whereas the aliquots for sialic acids were hydrolyzed with 2 M acetic acid. After hydrolysis, the digests were dried under a stream of nitrogen gas, dissolved with $H_2O$, sonicated for 5 min on ice and transferred to injection vials.

A mix of neutral and amino sugar standards, and sialic acid standards with known number of moles were hydrolyzed in the same manner and at the same time as the samples. Four concentrations of standard mixtures (neutral and amino sugars, and sialic acids) were prepared to establish a calibration equation. The number of moles of each monosaccharide in the sample was quantified by linear interpolation of residue area units into the calibration equation.

The monosaccharides were analyzed by HPAEC using a Dionex ICS3000 system equipped with a gradient pump, an electrochemical detector, and an autosampler. The individual neutral and amino sugars, and sialic acids were separated by a Dionex CarboPac PA20 (3×150 mm) analytical column with an amino trap. The gradient program used the following mobile phase eluents: for neutral and amino sugars, degassed nanopure water and 200 mM NaOH; For sialic acids, 100 mM NaOH and 1 M sodium acetate in 100 mM NaOH. Injection was made every 40 min for neutral and amino sugars and every 35 min for sialic acids.

Two samples were then analyzed for certain glycan residues with results presented in Table 7.

TABLE 7

Glycosyl Residue Identifications and Measurements on Transient Sialylated Products

| Sample ID | Glycosyl Residue | Total Residues in Sample Hydrolyzed nanomoles | %, by Mole | |
|---|---|---|---|---|
| | | | µg | |
| 1 | Fucose (Fuc) | 2.98 | 18.14 | 3.44 |
| | N-acetyl galactosamine (GalNAc) | nd | — | — |
| | N-acetyl glucosamine (GlcNAc) | 36.61 | 165.52 | 42.26 |
| | Galactose (Gal) | 12.39 | 68.77 | 14.30 |
| | Glucose (Glc) | nd | — | — |
| | Mannose (Man) | 18.46 | 102.46 | 21.31 |
| | N-acetyl neuraminic acid (NANA) | 16.19 | 52.35 | 18.69 |
| | N-glycolyl neuraminic acid (NGNA) | nd | — | — |
| 2 | Fucose (Fuc) | 0.40 | 2.45 | 3.66 |
| | N-acetyl galactosamine (GalNAc) | nd | — | — |
| | N-acetyl glucosamine (GlcNAc) | 4.25 | 19.21 | 38.80 |
| | Galactose (Gal) | 1.36 | 7.55 | 12.42 |
| | Glucose (Glc) | nd | — | — |
| | Mannose (Man) | 2.89 | 16.03 | 26.36 |
| | N-acetyl neuraminic acid (NANA) | 2.05 | 6.64 | 18.76 |
| | N-glycolyl neuraminic acid (NANA) | nd | — | — |

1, 2 Dialyzed aliquots hydrolyzed from each sample was ~200 µg for neutral & amino sugars and ~200 µg for sialic acids.

Fucose, N-acetylglucosamine, galactose and mannose were detected in all four samples. Among the sialic acids, NANA was detected in all four glycoproteins.

Example 7: Production of Sialylated Tetramer Form of rBuChE

Sialylation of rBuChE can be achieved using either (a) transient or (b) transgenic strategies. Transient strategies (a) involve the co-transfection of pBCHEKBP007 alone, or with proline rich adhesion domain (PRAD) peptide expressing vectors (as described above for monomeric or tetrameric product, respectively), along with the pICH88266 plant expression vector in appropriate *Agrobacterium* stains. The pICH88266 plasmid contains expression constructs for the seven genes to allow sialic acid to be synthesized, functionalized and transferred to nascent glycan strains in the plant Golgi apparatus along with the BAR selectable marker gene.

For transient expression of the Tetramer-sialylated rBuChE in plants, the "magnifection" (Icon Genetics GmbH, Halle/Saale, DE) procedure was used with minor modifications. Plants grown for 24-26 days in an enclosed growth room at 22-24° C. were used for vacuum infiltration. Overnight-grown *Agrobacterium* cultures for rBuChE (Vector ID: pBCHEKBP007), the tetramerizing peptide from ColQ (Vector ID: Tetra 4; [both ColQ and Lamellipodin vectors where shown to work similarly in other studies]) and the sialylation pathway (Vector ID: pICH88266) were mixed in the infiltration buffer (10 mM MES, 10 mM $MgSO_4$, pH 5.5). The vector pPBCHKBP007 was diluted 1:1000 (*Agrobacterium* cells:buffer), Tetra 4 was diluted 1:200 (*Agrobacterium* cells:buffer) and pICH88266 was diluted 1:10 (*Agrobacterium* cells:buffer). The infiltration solution was transferred into custom built (Kentucky Bioprocessing, Owensboro, Ky.) vacuum chambers. The aerial parts of entire plants were submerged upside down into the bacterial/buffer solution and a vacuum of 24" of mercury was applied for 2 min and released. For 80 kg of harvested plant biomass 280 L of infiltration solution was made requiring 280 mL of vector pBCHEKBP007, 1.4 L of vector Tetra 4 and 28 L of vector pICH88266. Post infiltration, plants were returned to the growth room under standard growing conditions. Harvest of the aerial parts of the entire plants occurred at 7 dpi (days post infiltration).

A scalable extraction, clarification, and non-affinity purification methodology was developed to purify the inventive tetramer rBuChE. Enzyme extraction was accomplished using mechanical disintegration of infected biomass in the presence of a phosphate buffer. The initial extract was clarified using pH shifting followed by depth filtration employing a plate/frame filter press and diatomaceous earth filter aid. The rBuChE was captured from the clarified extract using Capto Adhere™ multimodal resin (GE Healthcare), with elution accomplished using decreasing pH. The eluent from the capture step was then diluted to low conductivity and applied to Ceramic Hydroxyapatite (CHT) Type I multimodal resin (Bio-Rad Laboratories). The rBuChE was eluted from CHT using an increasing sodium chloride gradient, with host proteins stripped from the column using a high concentration of sodium phosphate. The CHT eluent was incubated with 1% v/v Triton X-114, followed by heating to produce a precipitated detergent phase that contained the majority of endotoxin. The aqueous phase (supernatant) was then removed from the detergent phase and diluted to low conductivity in preparation for final polishing. Residual detergent was removed by binding the rBuChE onto Capto Q™ strong anion exchange resin (GE Healthcare), followed by extensive washing with buffer to fully flush the detergent from the column. Elution of rBuChE from Capto Q was accomplished using an increasing sodium chloride gradient. The Capto Q eluent was then diafiltered into phosphate-buffered saline containing arginine, followed by concentration to at least 25 mg/mL using tangential flow ultrafiltration. The bulk drug substance was sterilized using 0.2 μm filtration and stored at 2-8° C. Final product properties are shown in FIG. 14.

Example 8: Production of Transgenic Sialylating SIAL-NbRNAiΔXF Plant Line from ΔXTFT *N. benthamiana* Plants Transgenic strategies have been developed for exogenous gene sialylation by transforming the genes from the pICH88266 vector into the NbRNAiΔXF plant strain to produce SIAL-NbRNAiΔXF plant lines. The strategy used is detailed in FIG. 11. PCR methodologies and Western blotting using *Sambucus nigra* lectin (SNA) lectin were used to screen lines and select for homozygocity. FIG. 20 summarizes plant line selection. T1 and T2 progeny have been identified that have intact genetic loci (by PCR analysis) and glycosylation phenotype (e.g., the presence of sialic acid residues on secreted proteins as determined by binding by the SNA that binds terminal sialic acid on glycan chains). These plant lines are currently under breeding programs to develop homozygous, stable transgenic lines expressing all eight gene products showing functional recombinant protein sialylation. Homozygous seed was then produced from the selected SIAL-NbRNAiΔXF-88266#11 line as detailed in FIG. 21.

Nb SIAL-NbRNAiΔXF seed was mixed for production due to small amount of seed from each lines and the extensive production required. The amounts were equal upon weight, but each line could have different efficiencies—higher or lower of sialylation activity. The pooled plant from seed and Nb SIAL-NbRNAiΔXF-8266#11 in particular were infiltrated with Agrobacteria harboring the BuChE viral expression construct (pICH92631) at a 1:1000 dilution. Prior purification, crude plant extracts (100 mg plant tissue extracted in 0.3 ml 0.2 M citrate buffer pH6 supplemented with 1 mM EDTA) from harvested 7 dpi plant tissue were pretested for BuChE activity using an Ellman assay. After this pretest, the His-tagged BCHE was purified from the different samples using Ni-NTA chromatography. Comparable amounts of purified BCHE (~2 μg each) were separated on polyacrylamide gels supplemented with SDS, blotted on PVDF membranes and probed with biotinylated SNA lectin (*Sambucus nigra* lectin; Vector laboratories, Peterborough, UK) and streptavidin-HRP conjugate (Life Technologies, Darmstadt, Germany) for detection of sialic acid. To confirm the detection of sialylated rBuChE, the membranes were stripped and re-probed with a goat anti-BCHE polyclonal antibody (Santa Cruz Biotechnology, Heidelberg, Germany) and anti-goat IgG-peroxidase conjugate (Sigma-Aldrich, St. Louis, USA).

Sialylation of rBuChE was detected within many plants from the NbRNAiΔXF-88266#11 line (FIG. 12 and FIG. 21). Thus, the transgenic approach was understood to be a possible pathway to produce sialylated rBuChE. From earlier examples, it was expected that transfection of NbRNAiΔXF-88266#11 plants with *Agrobacterium* cultures for rBuChE (Vector ID: pBCHEKBP007), the tetramerizing peptide from ColQ (Vector ID: Tetra 4; [both ColQ and Lamellipodin vectors were shown to work similarly in other studies]) has been determined to produce a tetramerized and sialylated rBuChE product. The increased size of the tetramerized product and its similarity to serum-based BuChE in terms of sialylation was also predicted to produce a superior product for nerve agent scavenging due to improved PK performance in mammals.

Nb SIAL-NbRNAiΔXF seed was planted and tested for sialylation capability using the SNA Western blot methodology. FIG. 22 provides the particular plant lines derived from original transformants Nb SIAL-NbRNAiΔXF-11 and -5. SIAL-NbRNAiΔXF-11 and -5 progeny plants (T2 generation) and controls (Benz) were grown and infected with a 1:1000 dilution of pBCHEKBP007 and a 1:200 dilution of Tetra 4 vectors and harvested 7 dpi. The plants were extracted for SNA and BCHE western blot analysis.

1. Negative Control Benz
2. Negative Control Transgenic
3. NBG 41 with pBCHEKBP007 and Tetra Peptide 4
4. NBG 42 with pBCHEKBP007 and Tetra Peptide 4
5. NBG 43 with pBCHEKBP007 and Tetra Peptide 4
6. NBG 45 with pBCHEKBP007 and Tetra Peptide 4
7. NBG 46 with pBCHEKBP007 and Tetra Peptide 4
8. NBG 47 with pBCHEKBP007 and Tetra Peptide 4

Extractions were performed using a 2:1 buffer to biomass ratio. 45 mL of green juice was immediately centrifuged to produce a S1 sample. S1 pellets were produced at 1000×g for 10' at 4° C. 1000 μL of S1 was centrifuged at 16000×g for 2' to produce an S2. Reduced NuPAGE samples were prepared and gels ran at 200V, 50'. The results and loading order are provided in FIG. 13.

These data demonstrate that six sialylation transgenic seed lines grown in 104 cell trays show strong expression of rBuChE and the rBuChE and other protein bands show strong reactivity with the SNA lectin indicating that the sialylation system is intact and function in all T2 lines (FIG. 22). From these data, a pooled seed population was used to produce sialylated rBuChE in transgenic lines for analysis and testing.

Further breeding and selection continues for T3 lines expected to show more stability with regards to sialylation pathway. Seed stock designation Nbg-45 and Nbg-43 (both from initial sialic acid transgenic plant Nb88266-11) were surface sterilized using ethanol and sodium hypochlorite then plated onto Murashige and Skoog media plus Gamborg's vitamins plates supplemented with the herbicide Phosphinothricin. Phosphinothricin resistance serves as a marker gene in the transgenic system. Plants that germinate and remain green contain the marker gene and suggest the sialylation gene cassette is intact. Germination and Phosphinothricin results were recorded ten days post sowing (dps) with all plants thriving and green. Plants were transplanted from the media plates to soilless plant media in five gallon pots for seed production. Thirteen pots were established for plants from seed stock Nbg-45 and 12 pots for Nbg-43.

Seed pod collection on plants commenced 61 days posttransplant. Per the standard seed production protocol, seed pods from individual plants are collected over a period of one to two weeks then moved to light carts to complete the pod drying process. Seeds were then cleaned and sized through a sieving process. Seed too small or too big was understood to be possibly retained for research purposes, but the seed retained by the proper sized sieve was that which was qualified. This harvest, drying and cleaning step was repeated over the entire harvesting time period. The cleaned seed was bulked together by individual plants and is kept separate until sufficient testing concludes that seed from individual plants can be bulked together. Typical N. benthamiana ΔXF seed lot testing includes germination, vigor, morphology, and nptII tests (indicative of kanamycin resistance marker gene). Specific testing for sialic acid transgenic seed lines was undertaken in relation to the following protocol:

1. Germination on Phosphinothricin media plates. If segregation for Phosphinothricin was recorded the seed from segregating plants was not bulked with seed from non-segregating plants.
2. If Phosphinothricin media results are 100% positive plantlets were transferred to pots containing soilless media and grown until large enough to syringe IF with a his-tagged BuChE vector. Extracts of IF spots were performed, followed by BuChE enrichment using magnetic beads (Dynabeads® His-Tag Isolation and Pulldown). Anti-BuChE Westerns and SNA blots were performed for determinations of the presence of BuChE and sialylation. If segregation for sialylation was recorded, seed from a segregating plant was not bulked with seed from non-segregating plants.

Seed lots that tested 100% positive for the Phosphinothricin herbicide selection and the BuChE/SNA Western (along with germination, vigor, morphology and nptII) tests were bulked together and approved for use in future BCHE production runs. Prior to large scale use seed (all or a portion) was pelleted to facilitate ease of use with an automated seeding system.

Approximately 200 g of seed was collected with approximately 75 g cleaned and sieved (3 g per plant×25 plants=75 g). Seed collection continued for another six to eight weeks until it was shown that the predicted estimate of approximately 600-800 grams of seed was produced within a final bulked seed lot (with all 25 plants combined). Such a seed quantity can potentially produce 7.2-9.6 million plants demonstrating the scalability and robustness of the transgenic strategy for production.

Example 9: Production of Tetrameric rBuChE in Transgenic Sialylating SIAL-NbRNAiΔXF Plant Lines Tetramer formation for the rBuChE plant-based products was undertaken through the utilization of the following Vectors:

rBuChE: pBCHEKBP007 (1:1000 dilution),
PRAD peptide 4: Tetra 4 (1:200 dilution)
Nb SIAL-NbRNAiΔXF seed was mixed for production due to small amount of seed from each lines and the extensive production required. The amounts were equal in terms of weight, but each line could have different efficiencies in terms of higher or lower sialylation activity. For transient expression of the tetramer-sialylated rBuChE in plants, the magnifection procedure was again used with minor modifications. Plants grown for 24-26 days in an enclosed growth room at 22-24° C. were used for vacuum infiltration. Overnight-grown Agrobacterium cultures for rBuChE (Vector ID: pBCHEKBP007), the tetramerizing peptide from ColQ (Vector ID: Tetra 4) and the sialylation pathway (Vector ID: pICH88266) were mixed in the infiltration buffer (10 mM IVIES, I0 mM $MgSO_4$, pH 5.5). The vector pPBCHKBP007 was diluted 1:1000 (Agrobacterium cells:buffer), Tetra 4 was diluted 1:200 (Agrobacterium cells:buffer) and pICH88266 was diluted 1:10 (Agrobacterium cells:buffer). The infiltration solution was transferred into vacuum chambers. The aerial parts of entire plants from Nicotiana benthamiana SIAL-NbRNAiΔXF pooled seed were submerged upside down into the bacterial/buffer solution and a vacuum of 24" of mercury was applied for 2 minutes and released. For 80 kg of harvested plant biomass, 280 L of infiltration solution was made requiring 280 mL of vector pBCHEKBP007, 1.4 L of vector Tetra 4, and 28 L of vector pICH88266. Post infiltration, plants were returned to the growth room under standard growing conditions. Harvest of the aerial parts of the entire plants occurred at 7 dpi.

A scalable extraction, clarification, and non-affinity purification methodology was developed to purify the tetramersialylated rBuChE products. Enzyme extraction was accomplished using mechanical disintegration of infected biomass in the presence of a phosphate buffer. The initial extract was clarified using acidic pH shifting followed by depth filtration employing a plate/frame filter press and diatomaceous earth filter aid. The rBuChE was captured from the clarified extract using Capto Adhere™ multimodal resin (GE Healthcare), with elution accomplished using decreasing pH. The eluent from the capture step was then diluted to lower conductivity and applied to Ceramic Hydroxyapaptite (CHT) Type I multimodal resin (Bio-Rad Laboratories). The rBuChE was eluted from CHT using an increasing sodium chloride gradient, with host proteins stripped from the column using a high concentration of sodium phosphate. The CHT eluent was incubated with 1% v/v Triton X-114, followed by heating to produce a precipitated detergent phase that contained the majority of endotoxin. The aqueous phase (supernatant) was then removed from the detergent phase and diluted to lower conductivity in preparation for final polishing. Residual detergent was removed by binding the rBuChE onto Capto Q™ strong anion exchange resin (GE Healthcare), followed by extensive washing with buffer to fully flush the detergent from the column. Elution of rBuChE from Capto Q was accomplished using an increasing sodium chloride gradient. The Capto Q eluent was then diafiltered into phosphate-buffered saline containing arginine, followed by concentration to at least 25 mg/mL using tangential flow ultrafiltration. The bulk drug substance was sterilized using 0.2 μm filtration and stored at 2-8° C.

The binding of OPs agents was compared between the transgenically sialylated rBuChE and plasma-derived BuChE. A continuous method of assessing inhibition constants (with butyrylthiocholine in a modified Ellman assay) was used to determine $k_i$ values of OPs nerve agents with KBP BuChE, as compared to human plasma-derived BuChE. As shown in FIG. 14, there was no statistical difference between the plant-produced rBuChE and plasma-derived BuChE with regards to binding any tested OPs nerve agents.

Also shown in FIG. 14, the different BuChE products noted above, ranging from dimer, oligomer, and plasma-derived types, in comparison with the plant-derived tetramer sialylated rBuChE of the invention, were measured for their ability to inhibit OPs effects. As an example, the graphs provided show the comparative measure of the binding of the sialylated rBuChE tetramer purified from transgenic plants and indicate the similarity in binding constants between plant-produced rBuChE and plasma-derived BuChE. In these experiments, the higher the inhibition constant indicates the better the result. The inventive plant-derived product equaled or bested the plasma-derived compound for each organophosphorus species (GA, GB, GD, GF, VX, and VR, specifically). With the comparative ease in manufacture and far lower expense, as well as the generally higher yield capacity of plant-based products and, again, the transgenic capabilities for scalability and continuous supply, it is evident that the plant-based methods provide highly effective results in this manner.

Example 10: Glycan Analysis of Transgenically Sialylated rBuChE

Further analysis was undertaken of the glycan constituents on the tetramerized sialylated rBuChE plant-derived product. The glycan structures were basically analyzed for content and whether the transient production scheme accorded effective and high occupancy measurements for optimal OPs effectiveness.

An intact aliquot of each sample was allocated for neutral and amino sugars analysis (~200 μg), and for sialic acids analysis (~200 μg). The aliquots for neutral and amino sugars were hydrolyzed with 2.0 N trifluoroacetic acid (TFA), whereas the aliquots for sialic acids were hydrolyzed with 2 M acetic acid. After hydrolysis, the digests were dried under a stream of nitrogen gas, dissolved with $H_2O$, sonicated for 5 min on ice and transferred to injection vials.

A mix of neutral and amino sugar standards, and sialic acid standards with known number of moles were hydrolyzed in the same manner and at the same time as the samples. Four concentrations of standard mixtures (neutral and amino sugars, and sialic acids) were prepared to establish a calibration equation. The number of moles of each monosaccharide in the sample was quantified by linear interpolation of residue area units into the calibration equation.

The monosaccharides were analyzed by HPAEC using a Dionex ICS3000 system equipped with a gradient pump, an electrochemical detector, and an autosampler. The individual neutral and amino sugars, and sialic acids were separated by a Dionex CarboPac PA20 (3×150 mm) analytical column with an amino trap. The gradient program used the following mobile phase eluents: for neutral and amino sugars, degassed nanopure water and 200 mM NaOH; for sialic acids, 100 mM NaOH and 1 M sodium acetate in 100 mM NaOH. Injection was made every 40 min for neutral and amino sugars and every 35 minutes for sialic acids. Table 11, below, provides the analytical results.

The N-glycans were further analyzed subsequent to cleavage from the tetramer products. Such N-glycans cleavage was generated through by enzymatic activity with a solution of PNGase A for 24 hours at 37° C. then PNGase F for another 24 hours at 37° C. The released N-glycans were then purified with a C18 SPE cartridge. The carbohydrate fraction was eluted with 5% acetic acid and dried by lyophilization. The N-linked oligosaccharides were further permethylated (based on a method described by Anumula and Taylor, 1992). The glycans were dried with nitrogen gas and profiled, as described above, by NSI-FTMS.

As above, such analysis was determined using a LTQ Orbitrap XL mass spectrometer (ThermoFisher) equipped with a nanospray ion source. Permethylated N-linked glycans were dissolved in 1 mM NaOH in 50% methanol then infused directly into the instrument at a constant flow rate of 0.5 μL/min. A full FTMS spectrum was collected at 30 000 resolution with 3 microscans. The capillary temperature was set at 210° C. and MS analysis was performed in the positive ion mode. For total ion mapping (automated MS/MS analysis), m/z range, 200 to 2000 was scanned with ITMS mode in successive two mass unit windows.

Numerous N-glycans were found in the sample. These primarily were biantennary complex-type glycans with smaller amounts of high mannose glycosylation and hybrid-type glycosylation. FIG. 23 shows the summarized glycans found in this sample included proposed structures and the results of MS/MS analysis as part of total-ion-mapping (TIM).

Truncated or damaged glycans found in the sample are denoted in FIG. 23 in bold text. A number N-glycans found in the samples were originally assigned as common then reassigned as different truncated structures following the results of TIM mapping.

Further tests were undertaken for enhanced glycan analysis of the transgenically sialylated rBuChE products. Initially, such activities involved hydrolysis and analysis of the samples for monosaccharide identification and measurement determinations. To that end, aliquots of each sample were allocated for neutral and amino sugars and for sialic acids analyses, dried and weighed to determine the actual amounts of samples being used for analysis. The aliquots for neutral and amino sugars were hydrolyzed with 2.0 N trifluoroacetic acid (TFA), whereas the aliquots for sialic acids were hydrolyzed with 2 M acetic acid. After hydrolysis, the digests were dried under a stream of nitrogen gas, dissolved with $H_2O$, sonicated for 5 min on ice and transferred to injection vials.

A mix of neutral and amino sugars standards, and sialic acids standards with known amounts were hydrolyzed in the same manner and at the same time as the samples. Four concentrations of standard mixtures (neutral and amino sugars, and sialic acids) were prepared to establish a calibration equation. The amount and number of moles of each monosaccharide in the sample was quantified by linear interpolation of residue area units into the calibration equation.

The monosaccharides were analyzed by HPAEC using a Dionex ICS3000 system equipped with a gradient pump, an electrochemical detector, and an autosampler. The individual neutral and amino sugars, and sialic acids were separated by a Dionex CarboPac PA20 (3×150 mm) analytical column with an amino trap. The gradient program used the following mobile phase eluents: for neutral and amino sugars, degassed nanopure water and 200 mM NaOH; for sialic acids, 100 mM NaOH and 1 M sodium acetate in 100 mM NaOH. Injection was made every 40 min for neutral and amino sugars and every 35 min for sialic acids. The results are provided in Table 13 for two samples (Lots 4 and 5).

TABLE 13

Monosaccharide composition analysis of rBuChE glycoproteins by HPAEC-PAD.

| rBuChE | Glycosyl Residue | Total Residues in Sample Hydrolyzed µg | nanomoles | %, by mole |
|---|---|---|---|---|
| Lot 4 | Fucose (Fuc) | 1.30 | 7.95 | 5.60 |
| | N-acetyl galactosamine (GalNAc) | nd | — | — |
| | N-acetyl glucosamine (GlcNAc) | 9.93 | 44.91 | 31.67 |
| | Galactose (Gal) | 4.12 | 22.86 | 16.12 |
| | Glucose (Glc) | nd | — | — |
| | Mannose (Man) | 9.03 | 50.09 | 35.32 |
| | N-acetyl neuraminic acid (NANA) | 4.95 | 16.00 | 11.29 |
| | N-glycolyl neuraminic acid (NGNA) | nd | — | — |
| Lot 5 | Fucose (Fuc) | 1.06 | 6.48 | 3.40 |
| | N-acetyl galactosamine (GalNAc) | nd | — | — |
| | N-acetyl glucosamine (GlcNAc) | 14.13 | 63.89 | 33.57 |
| | Galactose (Gal) | 6.56 | 36.38 | 19.11 |
| | Glucose (Glc) | nd | — | — |
| | Mannose (Man) | 11.77 | 65.30 | 34.31 |
| | N-acetyl neuraminic acid (NANA) | 5.66 | 18.29 | 9.61 |
| | N-glycolyl neuraminic acid (NGNA) | nd | — | — |

[1]Intact aliquots hydrolyzed from Lot: 14B002 was ~245 µg for neutral & amino sugars and ~245 µg for sialic acids, and from Lot: 14B003 was ~370 µg for neutral & amino sugars and ~370 µg for sialic acids From these results, it is evident that of the residues analyzed, N-acetylglucosamine, galactose and mannose were detected within both samples (lots). Also, the sialic acid, NANA, was detected in both samples.

From such overall data for the transiently and transgenically sialylated rBuChE products (tetramerized or not), the following observations have been made:

From four transgenic production rBuChE batches analyzed, three show 70-73% terminal sialic acid occupancy and one shows 50%. All sugars are present at reasonable molar ratios. It was not determined how a low occupancy level was present within a sample.

The transient sample showed 100% sialic acid occupancy with unnatural molar ratios of sugars, possibly due to sugar cleavage and instability (previous data showed 70% occupancy).

Pooled transgenic T2 seed lot sialylates were found to be at a level similar to the transient system.

Transient strategies show occupancy in 6 of 9 potential sites while the transgenic approach shows glycan occupancy on 8 of 9 sites with the last site problematic. Thus, the transgenic approach appears to be superior and more complete for glycosylation.

Thus, overall, it is evident not only our plant-based rBuChE production methods suitable to provide highly effective OPs protections in mammals (whether delivered intravenously or intramuscularly), but the ability to produce the tetramer form thereof as well as highly sialylated structures reliably and to a necessary scalable level, but such products may also be provided through seed lines for a continuous reliable supply, as well.

Example 11: Pilot and Definitive Pharmacokinetic Studies of rBuChE Produced in Plant System Two PK studies were performed in male Hartley guinea pigs to evaluate the characteristics of rBuChE. Complete details of these studies are presented in the final reports for SRI Study Nos. B616-13 and B618-13 which are provided in Appendices IV and V. First, a pilot study was conducted that compared three different forms of rBuChE: the neat monomer (Lot 13B001), a sialylated monomer dimer (Lot 13B002), and a sialylated tetramer (Lot 13B003) administered by the intravenous (IV) route. Table 14 presents the design for the pilot study (SRI Study No. B616-13) (with the expectation that a suitable pilot study result would lead to a more definitive test strategy).

TABLE 14

| Overall PK Testing Strategy | | | | | | | | |
|---|---|---|---|---|---|---|---|---|
| Group | rBuChE Variant | Activity (U/mg) | Dose (mg/kg; U/kg) | Dose Conc. (mg/mL) | Dosing Volume (mL/kg) | Dose Route [a] | No. of Animals | Plasma Collection Time Points [b, c] |
| 1 | A (Neat Monomer) | 285 | 25 (7125) | 17.6 | 1.43 | IV | 3 | Pre-dose, 5, 10, 20, 30, 60 min, 2, 4, 8, 24, 36, 48, 72, 120 and 168 hr |
| 2 | B (Monomer Dimer Sialylated) | 338 | 25 (8450) | 30.8 | 0.82 | IV | 3 | Pre-dose, 5, 10, 20, 30, 60 min, 2, 4, 8, 24, 36, 48, 72, 120 and 168 hr |
| 3 | C (Tetramer Sialylated) | 426 | 25 (10650) | 28.7 | 0.88 | IV | 3 | Pre-dose, 5, 10, 20, 30, 60 min, 2, 4, 8, 24, 36, 48, 72, 120 and 168 hr |

[a] Dose administration was via a jugular vein catheter (JVC).
[b] Blood was collected from the JVC port not used for dose administration. Due to loss of catheter patency in some of the animals, blood was also collected from methods approved on SRIs IACUC protocol 10006.
[c] Plasma samples were analyzed by the Ellman assay.

Next, the definitive PK study was performed using the sialylated tetramer (Lot 13B005) administered by both the IV and intramuscular (IM) routes. The decision to evaluate the sialylated tetramer in the definitive study was based on evaluation of PK characteristics determined in the pilot study as well as physicochemical properties analyses conducted at K8P throughout the continuous process development work. Table 15 presents the design for the definitive study (SRI Study No. B618-13).

TABLE 15

Study Design for Definitive Pharmacokinetic Study
of Sialylated Tetramer rBuChE in Guinea Pigs

| Group | Test Article | Activity (U/mg) | Dose Level (mg/kg; U/kg) | Dose Conc. (mg/mL) | Dosing Volume (mL/kg) | Dose Route | No. of Animals | Plasma Collection Time Points [a, b] |
|---|---|---|---|---|---|---|---|---|
| 1 | rBuChE (tetramer sialylated) | 525 | 25 (13125) | 28.0 | 0.89 | IV | 4 | Pre-dose, 5, 10, 20, 30, 60 min, 2, 4, 8, 24, 36, 48, 72, 120 and 168 hr |
| 2 | rBuChE (tetramer sialylated) | 525 | 25 (13125) | 28.0 | 0.89 | IM | 4 | Pre-dose, 5, 10, 20, 30, 60 min, 2, 4, 8, 24, 36, 48, 72, 120 and 168 hr |

[a] In Group 1, blood was collected from the JVC port not used for dose administration.
[b] Plasma samples were analyzed by the Ellman assay.

The basic test system undertaken was as follows:

Male Hartley guinea pigs were purchased from Charles River (Raleigh, N.C.), with either a single jugular vein catheter (JVC) or dual JVC by the vendor prior to shipment. The animals were five to six weeks and 320-409 grams in weight. General procedures for animal care and housing were in accordance with the National Research Council (NRC) Guide for the Care and Use of Laboratory Animals, 8th edition (2011) and the Animal Welfare Standards incorporated in 9 CFR Part 3, 1991. The animals were housed one per cage in hanging polycarbonate cages with hardwood chip bedding, using a 12 hr light/12 hr dark schedule, at 72-73° F., and at 33-46% humidity. The animal room had at least ten room volumes per hour ventilation, with no recirculation of air. Harlan Teklad Certified Guinea Pig chow (#2040C) was provided ad libitum. Feed was analyzed periodically to ensure that contaminants known to be capable of interfering with the study and reasonably expected to be present in such feed were not present at levels that would affect the study. Documentation of feed analyses is maintained in the study records. Water (purified, reverse osmosis) was provided ad libitum. Based on previous reports, no contaminants that could interfere with and affect the results of the study are expected to have been present in the water. Copies of annual analysis reports are maintained at SRI for reference. Animals were individually identified by an ear punch.

Study Procedures and Endpoints:

Dose administration was by the IV route (SRI Study Nos. B616-13 and B618-13) or IM route (SRI Study No. B618-13). Mortality and morbidity were checked at least once daily and clinical observations were recorded immediately post-dose on the day of dose administration, once daily thereafter, or more often as clinical signs warranted. Animals were examined for any altered clinical signs, including gross motor and behavioral activity, and observable changes in appearance. Body weights were determined one day before the start of the study for randomization and on Day 1 for dose administration calculations only. Blood was collected from the JVC port or other site approved by SRI's IACUC and ACURO, into a tube containing $K_3EDTA$, processed to plasma, and then stored frozen at $-70° \pm 10°$ C. Approximately 100 μL total whole blood (~50 μL of plasma) was collected from each guinea pig pre-dose, and at 5, 10, 20, 30, 60 min, 2, 4, 8, 24, 36, 48, 72, 120 and 168 hr post-dose.

Pharmacokinetic Analysis Procedures:

Data were subjected to non-compartmental analysis using WinNonlin® Model 200 (for extravascular administration) or Model 201 (for IV bolus administration); a uniform weighting factor was applied to each data set. $T_{max}$ and $C_{max}$ values were determined directly from the data. $AUC_{last}$ values were calculated using the log/linear trapezoidal (IV dose) or linear up/log down trapezoidal (IM dose). Values were calculated for each individual guinea pig. The dose administered was input to the program as U/kg, and as a result no additional corrections for individual body weights of the animals were necessary. The background levels of BuChE, determined for each animal from a sample collected prior to dose administration, were not subtracted from the measured plasma concentrations. The actual times recorded for sample collection were used through the first four hours for the calculations. The following parameters and constants were determined for the IV and IM groups: observed maximum plasma concentration ($C_{max}$), time to maximum plasma concentration ($T_{max}$), area under the plasma concentration-time curve to the last time point ($AUC_{last}$), area under the plasma concentration-time curve extrapolated to infinity ($AUC_{inf}$), terminal phase elimination half-life ($t_{1/2}$), mean residence time to extrapolated infinity ($MRT_{inf}$). The volume of distribution at steady state ($V_{ss}$) and clearance (Cl) were determined for the IV group only. Bioavailability (F) after IM administration was calculated using the $AUC_{last}$ values for both the IV and IM groups.

Clinical Observations:

Clinical observations showed that one animal from the tetramer sialylated rBuChE dose group was slightly hypoactive on Day 1. All other animals appeared normal throughout the study.

Plasma Drug Levels:

FIG. 15 presents the plasma profiles of the three rBuChE variants, which varied markedly. The data are presented as U/mL plasma. Variant A, the neat monomer, was cleared very rapidly from plasma and the concentration was below the background for BuChE after four hours. Variant B, the monomer dimer sialylated, was maintained in plasma at levels above background (1.05±0.185 U/mL) through 24 hr. Variant C, the tetramer sialylated, exhibited a biphasic plasma profile with a rapid distribution phase of about four to eight hours, followed by a longer elimination phase that extended for the entire time course of the study. Plasma concentrations of rBuChE were slightly above the background in the Variant C group at the final time point, 168 hours.

Pharmacokinetics Analysis Results:

The results of the PK analysis are presented in Table 16. The elimination half-life values ($t_{1/2}$,) varied markedly among the three forms of rBuChE. The neat monomer was eliminated from plasma with a $t_{1/2}$ of less than one hr (0.37 hr) while the monomer dimer sialylated had a $t_{1/2}$, about 20 fold longer, 7.5 hr. The longest $t_{1/2}$, was observed for the tetramer sialylated form, 60 hr. The MRT also varied with the form administered from 0.59 hr (Variant A) to 73 hr (Variant C). Cl was highest for Variant A (76.6 ml/hr/kg) and lowest for Variant C (6.27 mL/hr/kg). The highest concentrations of rBuChE were observed immediately after dose administration and were about 80 to 100 fold higher than the background. The neat monomer and monomer dimer sialylated variants had similar $C_{max}$ values, 98.8±2.8 U/mL and 91.3±16.2 U/mL, respectively. The tetramer sialylated variant had a lower mean $C_{max}$, 78.7±3.0 U/mL, despite the administration of a dose with higher activity than the other two variants. This difference was likely due to higher distribution of the tetramer sialylated as shown by the highest Vss of the three rBuChE forms. The more favorable parameters exhibited by the tetramer sialylated resulted in the highest exposure as shown by the AUC, 1704 hr·U/mL, about 18 and 7 fold higher than the $AUC_{inf}$ for the neat monomer and monomer dimer sialylated, respectively.

TABLE 16

Pilot Pharmacokinetic Parameters for rBuChE in Guinea Pigs [a]

| Guinea Pig | $C_{max}$ (U/mL) | $t_{1/2}$ (hr) | $AUC_{last}$ (hr · U/mL) | $AUC_{inf}$ (hr · U/mL) | Cl (mL/hr/kg) | VSS (mL/kg) | $MRT_{inf}$ (hr) |
|---|---|---|---|---|---|---|---|
| Neat Monomer, 25 mg/kg (7125 U/kg) | | | | | | | |
| 1 | 97.2 | 0.36 | 94.2 | 95.2 | 74.8 | 46.1 | 0.62 |
| 2 | 97.2 | 0.39 | 84.3 | 85.9 | 82.9 | 51.2 | 0.62 |
| 3 | 102 | 0.36 | 97.5 | 98.7 | 72.2 | 39.0 | 0.54 |
| Mean | 98.8 | 0.37 | 92.0 | 93.3 | 76.6 | 45.4 | 0.59 |
| SD | 2.8 | 0.02 | 6.9 | 6.6 | 5.6 | 6.1 | 0.05 |
| Monomer Dimer Sialylated, 25 mg/kg (8450 U/kg) | | | | | | | |
| 4 | 110 | 6.6 | 263 | 276 | 30.6 | 161 | 5.2 |
| 5 | 82.8 | 8.3 | 205 | 224 | 37.8 | 262 | 6.9 |
| 6 | 81.2 | 7.5 | 185 | 198 | 42.6 | 266 | 6.2 |
| Mean | 91.3 | 7.5 | 218 | 233 | 37.0 | 230 | 6.1 |
| SD | 16.2 | 0.9 | 41 | 40 | 6.0 | 60 | 0.9 |
| Tetramer Sialylated, 25 mg/kg (10650 U/kg) | | | | | | | |
| 7 | 80.4 | 45 | 1598 | 1701 | 6.30 | 354 | 57 |
| 8 | 80.4 | 74 | 1477 | 1799 | 5.90 | 529 | 89 |
| 9 | 75.2 | 62 | 1399 | 1611 | 6.60 | 490 | 74 |
| Mean | 78.7 | 60 | 1491 | 1704 | 6.27 | 458 | 73 |
| SD | 3.0 | 15 | 100 | 94 | 0.35 | 92 | 16 |

[a] Pharmacokinetic parameters were determined using plasma concentrations of BuChE that were not corrected for the background enzyme level. Mean BuChE activity in plasma was 1.05 ± 0.185 U/mL.

Pilot Study Conclusions:

Three variants of rBuChE were administered by the IV route to male guinea pigs. The dose of 25 mg/kg was well tolerated. The plasma profile and pharmacokinetic parameters varied markedly among the three proteins. Although the highest initial plasma concentration was observed for Variant A, the neat monomer, this form of rBuChE was rapidly eliminated from the plasma with a ty, and MRT of less than 1 hr and very rapid Cl, resulting in low plasma exposure. The pharmacokinetic characteristics most closely approximating those of human serum derived BuChE were observed for the tetramer sialylated form, which had a biphasic plasma profile, the highest $V_{ss}$, suggesting greater distribution of the protein, the lowest clearance (Cl), $t_{1/2}$ of 60 hr, and the highest exposure based on the AUC values for the three rBuChE variants.

From these promising results, it was then determined that a more definitive study was merited to analyze the potential benefits of the plant-derived rBuChE products.

Definitive Study Undertaking:

The same type of guinea pigs were utilized, kept, and tested as above, with a greater amount of rBuChE administered and actual treated subjects exposed to various OPs agents.

Mortality/Morbidity and Clinical Observations:

Clinical observations were collected and all animals appeared normal throughout the study.

Plasma Drug Levels:

FIGS. 16 and 17 show the plasma profile for rBuChE, in terms of U/mL and μg/mL, respectively, administered by the IV and IM routes. In the IV treatment group, rBuChE exhibited a biphasic plasma profile with a rapid distribution phase of about 4-8 hr, followed by a longer elimination phase that extended for the entire time course of the study. After IM administration, rBuChE activity in plasma was slightly above background at the first time point and then increased steadily until reaching a peak at 36 hr after dose injection. rBuChE was then was slowly eliminated. Plasma concentrations of rBuChE were above the background level, 0.911±0.197 U/mL, through the final blood collection time point at 168 hr after both IM and IV administration.

Pharmacokinetics Analysis:

The results of the pharmacokinetics analysis are presented in Table 17. In the IV group, the observed $C_{max}$ value was 63.5 U/mL, or about 70 fold higher than the background level. rBuChE was eliminated slowly from the plasma with a ty, of 63.4 hr and $MRT_{inf}$ of 83.5 hr for the IV group; this corresponded to a Cl of 9.8 mL/hr/kg. $V_{ss}$ was moderate, 836 mL/kg, suggesting extensive extracellular distribution. The $AUC_{last}$ and $AUC_{inf}$ were 1124 hr·U/mL and 1368 hr·U/mL, respectively. In the IM group, the observed $C_{max}$ value was 63.5 U/ml, ~8 fold greater than the background, and was observed at the $T_{max}$ of 36 hr. Both the ty, and $MRT_{inf}$ were longer than in the IV group, 86.5 hr and 142 hr, respectively. Exposure as shown by $AUC_{last}$ and $AUC_{inf}$ values was 689 hr·U/mL and 1005 hr·U/mL, respectively. The bioavailability (F) determined using $AUC_{last}$ was calculated to be 61.6±1.8%.

TABLE 17

Definitive Pharmacokinetic Parameters in Guinea Pigs of rBuChE Administered by IV and IM Routes

| Guinea Pig | $C_{max}$ (U/mL) | $T_{max}$ (hr) | $t_{1/2}$ (hr) | $AUC_{last}$ (hr · U/mL) | $AUC_{inf}$ (hr · U/mL) | Cl (mL/hr/kg) | $V_{ss}$ (mL/kg) | $MRT_{inf}$ (hr) | F (%)[a] |
|---|---|---|---|---|---|---|---|---|---|
| Intravenous group, 25 mg/kg (13125 U/kg) | | | | | | | | | |
| 1 | 60.7 | NA[b] | 61.3 | 978 | 1129 | 11.6 | 874 | 75.3 | NA |
| 2 | 68 | NA | 64.2 | 1181 | 1413 | 9.3 | 774 | 83.4 | NA |
| 3 | 62.5 | NA | 64.7 | 1097 | 1359 | 9.7 | 887 | 91.8 | NA |
| 4 | 62.7 | NA | 74.1 | 1241 | 1569 | 8.4 | 818 | 97.8 | NA |
| Mean | 63.5 | | 63.4 | 1124 | 1368 | 9.8 | 838 | 83.5 | |
| SD | 3.1 | | 1.8 | 114 | 182 | 1.3 | 52 | 8.3 | |
| Intramuscular group, 25 mg/kg (13125 U/kg) | | | | | | | | | |
| 5 | 7.7 | 36 | 82.6 | 694 | 997 | NC[c] | NC | 136 | 61.7 |
| 6 | 7.4 | 36 | 90 | 671 | 1036 | NC | NC | 151 | 59.7 |
| 7 | 7.5 | 36 | 87 | 711 | 1037 | NC | NC | 139 | 63.3 |
| 8 | 8 | 36 | 77.1 | 681 | 950 | NC | NC | 129 | 60.6 |
| Mean | 7.7 | 36 | 86.5 | 689 | 1005 | | | 142 | 61.6 |
| SD | 0.3 | 0 | 3.7 | 17 | 41 | | | 7.9 | 1.8 |

[a] Calculated using $AUC_{last}$ values
[b] NA, not applicable
[c] NC, not calculated Conclusions of the Definitive Study:

A single dose of a sialylated tetramer variant of rBuChE, 25 mg/kg (13125 U/mL), was administered to male Hartley guinea pigs by the IV and IM routes. The treatment was well tolerated and all animals appeared normal for the entire study, 168 hr after dosing. The enzyme exhibited PK parameters more closely comparable to those for human serum derived BuChE when compared to other recombinant moieties developed in this project. After IM administration, rBuChE was detected at levels slightly above the background at the first blood collection time point, with concentrations steadily increasing to a peak at 36 hr after injection. The $t_{1/2}$ values were 63.4 hr (IV) and 86.5 hr (IM), corresponding to a slow Cl, 9.8 mL/hr/kg, and $V_{ss}$, 836 ml/kg, that is consistent with extracellular distribution. The bioavailability of rBuChE after IM administration was about 60%.

Example 12: Efficacy Testing of Sialylated rBuChE Tetramer

Efficacy studies were conducted using three different nerve agents using a short time point IV model for protection.

GD and VX Nerve Agents

For these agents, there was administered an inventive plant-derived tetramer sialylated BuChE to male Hartley guinea pigs (300-350 grams) via an IV carotid catheter at 26.15 mg/kg for each subject.

After 15 minutes, animals administered 26.15 mg/kg were exposed to 3×LD50 of GD or VX via s.c. injection (n=6 for each).

GB Nerve Agent

For this agent, there was administered a plant-derived tetramer sialylated BuChE to male Hartley guinea pigs (300-350 grams) via an IV carotid catheter at 52.3 mg/kg.

After 15 minutes, animals administered 52.3 mg/kg were exposed to 3×LD50 of GB via s.c. injection (n=6).

In each situation, all of the test subject animals survived to 24 hours without any sign of OP intoxication.

These data demonstrate the efficacy potential of the sialylated tetrameric rBuChE to protect mammals from lethal nerve agent exposure. The attractive PK data suggest that this protection can be optimized by improvements in sialylation and tetramerizing efficiencies leading to a very competitively functioning product.

As alluded to above, such tetramerized and sialylated rBuChE products may also be utilized for other mammalian treatments, including neurological conditions (Alzheimer's), addiction therapies (for cocaine addictions treatments, for instance), and even enzyme replacement therapies to overcome BuChE deficiencies due to any number of genetic or other disorders. The viability of production in reliable fashion, particularly with high levels of sialylated glycans and tetramer formation, may further translate into effective mammalian (including human) treatment potential, as well.

Thus, the overall effectiveness of this newly discovered tetramer sialylated rBuChE product accords significant improvements within this industry. The further capability to produce such a new product through transgenic means, transfection processes, and other types of gene expression methodologies, thus opens up a notable area for not only OPs protections, but also other treatments for humans and other mammals that have heretofore been rather limited.

It should be understood that various modifications within the scope of this invention can be made by one of ordinary skill in the art without departing from the spirit thereof. It is therefore wished that this invention be defined by the scope of the appended claims as broadly as the prior art will permit, and in view of the specification if need be.

References cited hereinabove, are as follows:
1. Castilho et al., 2008. *Plant Physiol.* 147:331-9;
2. Castilho et al., 2010. *J Biol. Chem.* 285: 15923-30;
3. Castilho et al., 2011. *Glycobiol.* 21:813-82;
4. Castilho et al., 2011. *GlycoconjugateJ* 28:240
5. Diaz et al., Sensitive and specific detection of the non-human sialic Acid N-glycolylneuraminic acid in human tissues and biotherapeutic products. PLoS ONE 2009, 4:e4241
6. U.S. Pat. No. 8,729,245
7. Duysen et al., Wild-type and A328W mutant human butyrylcholinesterase tetramers expressed in Chinese hamster ovary cells have a 16-hour half-life in the circulation and protect mice from cocaine toxicity. *Pharmacol Exp Ther.* 2002 302:751-8.

8. Ellman, G. L. et al. [1961], *Biochem. Pharmacol.* 7:88-95
9. Engler et al., 2008, *PLoS One*, 3, e36472008
10. Giritch et al., 2006, *Proc. Natl. Acad. Sci. USA*, 103: 14701-14706
11. Geyer et al., PNAS, Nov. 23, 2010, vol. 107, no. 47, 20251-20256;
12. Gleba, Y., Klimyuk, V. & Marillonnet, S., 2005, *Vaccine* 23:2042-2048
13. Gleba, Y., Klimyuk, V. & Marillonnet, S. 2007, *Curr. Opin. Biotechnol.* 18:134-141
14. Ilyushina et al., Chemical polysialylation of human recombinant butyrylcholinesterase delivers a long-acting bioscavenger for nerve agents in vivo. *Proc Natl Acad Sci U S A.* 2013. 110:1243-8
15. Li et al., Lamellipodin proline rich peptides associated with native plasma butyrylcholinesterase tetramers. *Biochem. J.* (2008) 411, 425-432.
16. Schneider et al., 2014. *Plant Biotechnol. J* March 11. doi: 10.1111/pbi.12184;
17. Schneider et al., *Biotechnol J* 2014 April; 9(4): 501-10
18. Weber et al., 2011, *PLoS One*, 6, e16765
19. Werner et al., 2012, *Bioeng Bugs* 3, 38-43
20. Zheng et al., 2014. A highly efficient cocaine-detoxifying enzyme obtained by computational design. *NATURE COMMUNICATIONS* 15:3457|DOI: 10.1038/ncomms4457

---

SEQUENCE LISTING

<160> NUMBER OF SEQ ID NOS: 4

<210> SEQ ID NO 1
<211> LENGTH: 52
<212> TYPE: PRT
<213> ORGANISM: Nicotiana benthamiana
<220> FEATURE:
<221> NAME/KEY: Peptide
<222> LOCATION: (25)..(52)
<223> OTHER INFORMATION: Ras-associated and pleckstrin homology
    domains-containing peptide derived from Lamellipodin, associated
    with increased levels of tetramerized and sialylated recombinant
    butyrylcholinesterase; residues 1 to 24 are a barley alpha-amylase
    signal sequence.

<400> SEQUENCE: 1

Met Ala Asn Lys His Leu Ser Leu Ser Leu Phe Leu Val Leu Leu Gly
1               5                   10                  15

Leu Ser Ala Ser Leu Ala Ser Gly Ala Pro Ser Pro Pro Leu Pro Pro
            20                  25                  30

Pro Pro Pro Pro Pro Pro Pro Pro Pro Pro Pro Pro Pro Pro Pro Pro
        35                  40                  45

Pro Pro Leu Pro
    50

<210> SEQ ID NO 2
<211> LENGTH: 42
<212> TYPE: PRT
<213> ORGANISM: Nicotiana benthamiana
<220> FEATURE:
<221> NAME/KEY: Peptide
<222> LOCATION: (25)..(42)
<223> OTHER INFORMATION: Designed peptide; residues 1 to 24 are a barley
    alpha-amylase signal sequence.

<400> SEQUENCE: 2

Met Ala Asn Lys His Leu Ser Leu Ser Leu Phe Leu Val Leu Leu Gly
1               5                   10                  15

Leu Ser Ala Ser Leu Ala Ser Gly Ala Cys Cys Leu Leu Met Pro Pro
            20                  25                  30

Pro Pro Pro Leu Phe Pro Pro Pro Phe Phe
        35                  40

<210> SEQ ID NO 3
<211> LENGTH: 50
<212> TYPE: PRT
<213> ORGANISM: Nicotiana benthamiana
<220> FEATURE:
<221> NAME/KEY: Peptide
<222> LOCATION: (25)..(50)
<223> OTHER INFORMATION: Designed peptide; residues 1 to 24 are a barley -continued

```
     alpha-amylase signal sequence.

<400> SEQUENCE: 3

Met Ala Asn Lys His Leu Ser Leu Ser Leu Phe Leu Val Leu Leu Gly
1               5                   10                  15

Leu Ser Ala Ser Leu Ala Ser Gly Ala Cys Cys Leu Leu Met Pro Pro
            20                  25                  30

Pro Pro Pro Leu Phe Pro Pro Pro Phe Phe Asp Tyr Lys Asp Asp Asp
        35                  40                  45

Asp Lys
    50

<210> SEQ ID NO 4
<211> LENGTH: 70
<212> TYPE: PRT
<213> ORGANISM: Nicotiana benthamiana
<220> FEATURE:
<221> NAME/KEY: Peptide
<222> LOCATION: (25)..(70)
<223> OTHER INFORMATION: Acetylcholinesterase collagenic tail peptide
      derived from ColQ expressing increased levels of tetramerized and
      sialylated recombinant butyrylcholinesterase; resid 10. The method of claim 9, wherein said butyrylcholinesterase product exhibits at least 50% sialylation and greater than 50% tetramer formation.

11. The method of claim 10, wherein said butyrylcholinesterase product exhibits between 50%-73% sialylation and greater than 50% and up to 75% tetramer formation.

12. The method of claim 10, wherein said butyrylcholinesterase product exhibits at least 70% sialylation and at least 60% tetramer formation.

13. A recombinant butyrylcholinesterase product comprising a butyrylcholinesterase molecule associated with a polyproline adhesion domain permitting butyrylcholinesterase tetramer formation, wherein said recombinant butyrylcholinesterase product exhibits at least 50% sialylation and greater than 50% tetramer formation, the tetramerized product further comprising glycosylation sites and characterized by about 70% of glycosylation sites being bound to a single terminal sialic acid.

14. The recombinant butyrylcholinesterase product of claim 13, exhibiting between 50%-73% sialylation, and greater than 50% and up to 75% tetramer formation.

15. The recombinant butyrylcholinesterase product of claim 13, wherein said recombinant butyrylcholinesterase product exhibits at least 70% sialylation.

16. The recombinant butyrylcholinesterase product of claim 13, wherein said recombinant butyrylcholinesterase product exhibits at least 60% tetramer formation.

17. The recombinant butyrylcholinesterase product of claim 13, wherein said recombinant butyrylcholinesterase product is generated from plants or plant cells.

18. The recombinant butyrylcholinesterase product of claim 13, wherein said recombinant butyrylcholinesterase product is generated from plants or plant cells.

19. The recombinant butyrylcholinesterase product of claim 13, wherein said recombinant butyrylcholinesterase product is generated from plants or plant cells.

20. The recombinant butyrylcholinesterase product of claim 13, wherein said recombinant butyrylcholinesterase product is generated from plants or plant cells.

* * * * *